(12) United States Patent
Chen et al.

(10) Patent No.: US 11,664,189 B2
(45) Date of Patent: May 30, 2023

(54) APPARATUS OF CHARGED-PARTICLE BEAM SUCH AS SCANNING ELECTRON MICROSCOPE COMPRISING PLASMA GENERATOR, AND METHOD THEREOF

(71) Applicant: BORRIES PTE. LTD., Singapore (SG)

(72) Inventors: Zhongwei Chen, Los Altos Hills, CA (US); Xiaoming Chen, Sunnyvale, CA (US); Daniel Tang, Fremont, CA (US); Liang-Fu Fan, Fremont, CA (US)

(73) Assignee: BORRIES PTE. LTD., Singapore (SG)

( * ) Notice: Subject to any disclaimer, the term of this patent is extended or adjusted under 35 U.S.C. 154(b) by 0 days.

(21) Appl. No.: 17/662,655

(22) Filed: May 9, 2022

(65) Prior Publication Data

US 2022/0262596 A1    Aug. 18, 2022

Related U.S. Application Data

(63) Continuation-in-part of application No. 17/444,192, filed on Aug. 1, 2021, now Pat. No. 11,355,312.
(Continued)

(51) Int. Cl.
| | |
|---|---|
| *H01J 37/244* | (2006.01) |
| *H01J 37/20* | (2006.01) |
| *H01J 37/10* | (2006.01) |
| *H05H 1/46* | (2006.01) |
| *B08B 7/00* | (2006.01) |
| *H01J 37/28* | (2006.01) |
| *H01J 37/317* | (2006.01) |

(52) U.S. Cl.
CPC .......... *H01J 37/244* (2013.01); *B08B 7/0035* (2013.01); *H01J 37/10* (2013.01); *H01J 37/20* (2013.01); *H01J 37/28* (2013.01); *H05H 1/4645* (2021.05); *H01J 37/3174* (2013.01); *H01J 2237/24475* (2013.01); *H05H 2245/40* (2021.05)

(58) Field of Classification Search
CPC .......... H01J 37/244; H01J 37/10; H01J 37/20; H01J 37/28; H01J 37/3174; H01J 2237/24475; B08B 7/0035; H05H 1/4645; H05H 2245/40; A61L 2/14
See application file for complete search history.

(56) References Cited

U.S. PATENT DOCUMENTS

| | | | | |
|---|---|---|---|---|
| 11,094,499 B1* | 8/2021 | Chen | ................... | H01J 37/3174 |
| 2016/0003835 A1* | 1/2016 | Halbert | ................ | C12N 15/115 |
| | | | | 506/9 |

(Continued)

*Primary Examiner* — David A Vanore
(74) *Attorney, Agent, or Firm* — George Guosheng Wang; Upstream Research and Patent LLC

(57) ABSTRACT

The present invention provides an apparatus of charged-particle beam e.g. an electron microscope comprising a plasma generator for selectively cleaning BSE detector. In various embodiments, the plasma generator is located between a sample stage and a sample table having one or more openings or holes. The plasma generator generates plasma and distributes or dissipates the plasma through the openings of the sample table toward and onto surface of the BSE detector. Cleaning contaminants on the surface of the BSE detector frequently and selectively with in-situ generated plasma can prevent the detectors from performance deterioration such as losing resolution and contrast in imaging at high levels of magnification.

20 Claims, 18 Drawing Sheets

Related U.S. Application Data

(60) Provisional application No. 63/087,238, filed on Oct. 4, 2020.

(56) References Cited

U.S. PATENT DOCUMENTS

| | | | |
|---|---|---|---|
| 2016/0299103 A1* | 10/2016 | Saleh | H01J 37/32449 |
| 2017/0067838 A1* | 3/2017 | Anan | G01N 23/225 |
| 2018/0261422 A1* | 9/2018 | Kuramoto | H01J 37/3056 |
| 2022/0115204 A1* | 4/2022 | Chen | H01J 37/261 |
| 2022/0262596 A1* | 8/2022 | Chen | H01J 37/244 |

* cited by examiner

SARS-CoV-2

Figure 18

APPARATUS OF CHARGED-PARTICLE BEAM SUCH AS SCANNING ELECTRON MICROSCOPE COMPRISING PLASMA GENERATOR, AND METHOD THEREOF

CROSS-REFERENCE TO RELATED APPLICATIONS

This application is Continuation-in-Part of U.S. nonprovisional application Ser. No. 17/444,192 filed on Aug. 1, 2021 and docketed as "Elastic Connector," which claims the benefit under 35 U.S.C. Section 119(e) and Article 4 of the Stockholm Act of the Paris Convention for the Protection of Industrial Property of U.S. Provisional Patent Application No. 63/087,238, filed Oct. 4, 2020, entitled "Several Designs for Apparatus of Charged-Particle Beam and Methods Thereof," all of which are incorporated herein by reference in their entirety.

FIELD OF THE INVENTION

The present invention generally relates to a local plasma generator, and an apparatus of charged-particle beam such as a scanning electron microscope (SEM) using the same for electively cleaning one or more parts in the apparatus. Although the invention will be illustrated, explained, and exemplified by electron microscopes, it should be appreciated that the present invention can also be applied to other fields, for example, electron beam recorders, electron beam lithography systems, and the like.

BACKGROUND OF THE INVENTION

Owing to the small de Broglie wavelength of electrons, electron microscopes such as SEM, TEM and STEM can enable the user to examine fine detail as small as a single column of atoms. Therefore, electron microscopes find application in cancer research, virology, materials science as well as pollution, nanotechnology, and semiconductor research, and they are used to investigate the ultrastructure of a wide range of specimens including tumor cells, microorganisms, large molecules, biopsy samples, semiconductor device, metals, and crystals.

In a scanning electron microscope (SEM) or a scanning transmission electron microscope (STEM) that scans a specimen with an electron beam to obtain a magnified image of the specimen, secondary electrons, backscattered electrons (specimen backscattered electrons), specimen forward scattered electrons, and transmission electrons are obtained due to the interaction between the specimen and the irradiation primary electron beam. Depending on the relationship between the specimen and the detection position, the various kinds of electrons are discriminated when detected, and characteristic image contrasts are obtained by respective detectors, whereby a scanning magnified image of the specimen can be formed. The scanning transmission electron microscope (STEM) forms an image based on secondary electrons, forward scattered electrons, or transmission electrons that are produced from the specimen when scanned with a minute spot of an electron beam, and it has a subnanometer-size attainable resolution.

Back Scatter Electron (BSE) detectors are typically placed above the sample in the SEM sample chamber based on the scattering geometry relative to the incident beam. BSE detectors are solid-state devices, often with separate components for simultaneous collection of back-scattered electrons in different directions. Detectors above the sample collect electrons scattered as a function of sample composition, whereas detectors placed to the side collect electrons scattered as a function of surface topography.

However, the image quality begins to deteriorate because carbon contamination accumulates in the SEM chamber, particularly on the BSE detector, after many days of imaging. For example, the BSE detector of a SEM may be quickly contaminated with not only pump oils, fingerprints and improper vacuum practices, but also dirty specimens and decomposed biological samples (e.g. contamination from hydrocarbons) because of their proximity to the sample stage. Consequently, the performance of the detectors is deteriorated, for example, a loss of resolution and contrast in imaging at the highest levels of magnification. Collecting useful data from a sample after a period of time thus becomes tenuous. Frequently, it is necessary to clean or replace the BSE detector.

Advantageously, the present invention provides a new apparatus of charged-particle beam such as electron microscope with a local plasma generator that can solve the problems.

SUMMARY OF THE INVENTION

One aspect of the present invention provides an apparatus of charged-particle beam comprising a BSE detector, a plasma generator, and a sample stage system. The sample stage system includes an upper stage, a lower stage, and a sample table having one or more openings above the upper stage. The plasma generator is located below the sample table and sits onto or partially embedded into the upper sample stage. The BSE detector is located above the sample table. The sample table and the plasma generator are so configured that the plasma generator generates plasma and distributes or dissipates the plasma through the one or more openings of the sample table toward and onto surface of the BSE detector, to selectively "plasma clean" the BSE detector.

Another aspect of the present invention provides a method of selectively cleaning BSE detector in an apparatus of charged-particle beam, including a step of installing the plasma generator and making the apparatus as described above, and a step of generating plasma to selectively "plasma clean" the BSE detector.

The above features and advantages and other features and advantages of the present invention are readily apparent from the following detailed description of the best modes for carrying out the invention when taken in connection with the accompanying drawings.

BRIEF DESCRIPTION OF THE SEVERAL VIEWS OF THE DRAWINGS

The present invention is illustrated by way of example, and not by way of limitation, in the figures of the accompanying drawings and in which like reference numerals refer to similar elements. All the figures are schematic and generally only show parts which are necessary in order to elucidate the invention. For simplicity and clarity of illustration, elements shown in the figures and discussed below have not necessarily been drawn to scale. Well-known structures and devices are shown in simplified form, omitted, or merely suggested, in order to avoid unnecessarily obscuring the present invention.

FIG. 18 shows the image of a biological sample in a large FOV with low resolution and a small FOV with high resolution in accordance with an exemplary embodiment of the present invention.

DETAILED DESCRIPTION OF THE PREFERRED EMBODIMENT

In the following description, for the purposes of explanation, numerous specific details are set forth in order to provide a thorough understanding of the present invention. It is apparent, however, to one skilled in the art that the present invention may be practiced without these specific details or with an equivalent arrangement.

Where a numerical range is disclosed herein, unless otherwise specified, such range is continuous, inclusive of both the minimum and maximum values of the range as well as every value between such minimum and maximum values. Still further, where a range refers to integers, only the integers from the minimum value to and including the maximum value of such range are included. In addition, where multiple ranges are provided to describe a feature or characteristic, such ranges can be combined.

It is also to be understood that the terminology used herein is for the purpose of describing particular embodiments only, and it is not intended to limit the scope of the invention. For example, when an element is referred to as being "on", "connected to", or "coupled to" another element, it can be directly on, connected or coupled to the other element or intervening elements may be present. In contrast, when an element is referred to as being "directly on", "directly connected to", or "directly coupled to" another element, there are no intervening elements present.

Figure 1:
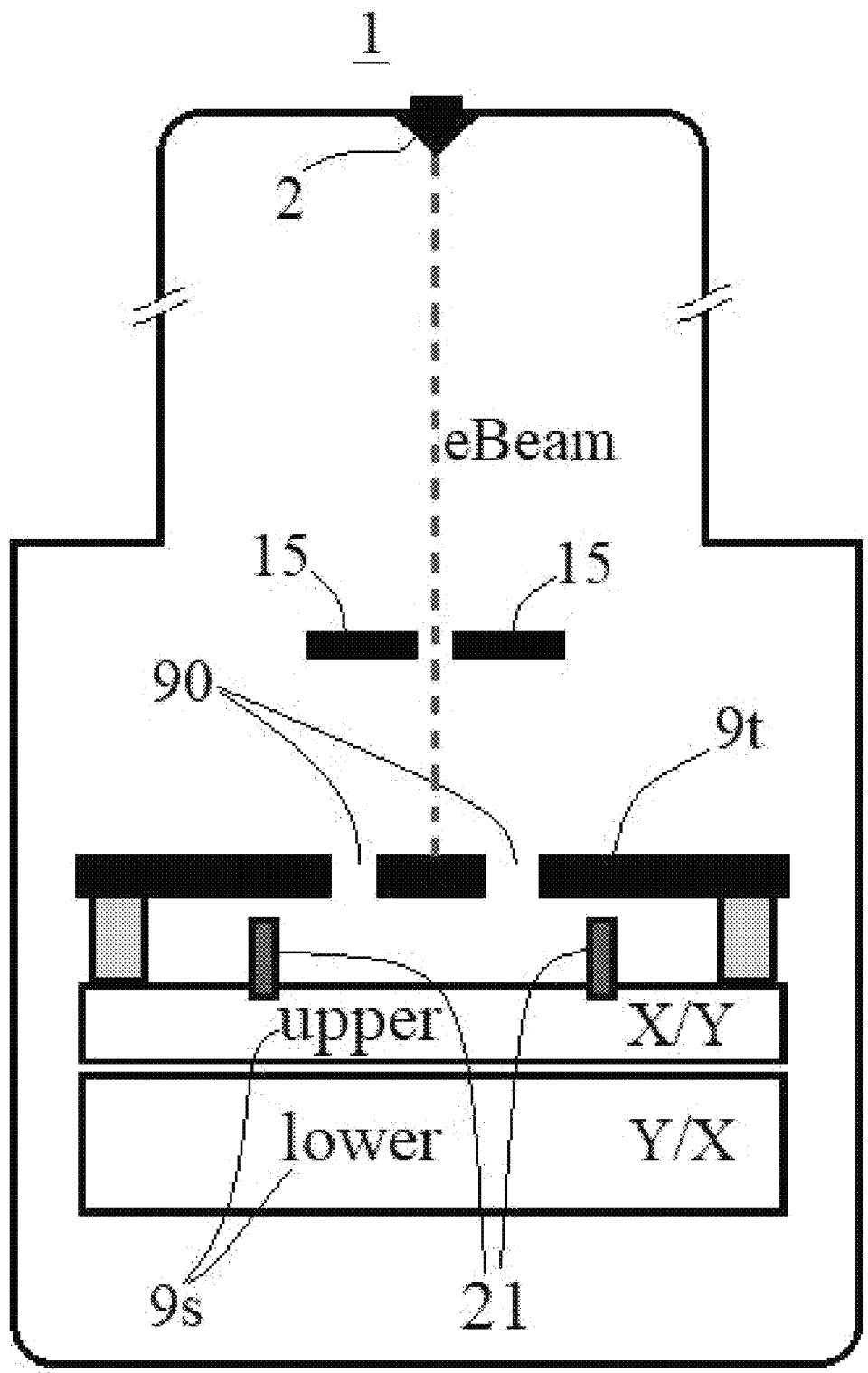
FIG. 1 schematically illustrates an apparatus of charged-particle beam comprising a plasma generator in accordance with an exemplary embodiment of the present invention.

With reference to FIG. 1, various embodiments of the invention provide an apparatus 1 of charged-particle beam comprising a BSE detector (or a SE detector) 15 located above a sample table 9t (as a part of a sample stage system) which is configured for placing a sample or a workpiece (not shown) thereon. Backscattered electrons (BSE) are reflected back by elastic interactions when the primary electron beam interacts with the sample. Secondary electrons (SE) come from the atoms of the sample as a result of inelastic interactions. BSEs and SEs contain different types of information. BSEs originate from deeper areas of the sample, while SEs come from surface regions. Images from BSEs display high sensitivity to differences in atomic numbers, which will show up as brighter or darker. SE images contain more detailed surface information.

For example, the apparatus 1 may be a scanning electron microscope (SEM). SEM images provide information on topography, composition, and morphology of the sample. BSE images provide valuable crystallographic, topographic and magnetic field information. Some SEMs can achieve resolution below 1 nm. Full sized instruments typically produce resolutions between 1 and 20 nm, while desktop models may produce resolutions of 20 nm or greater.

A SEM requires different types of detectors for backscattered and secondary electrons. The SE detector 15 may be an Everhart-Thornley detector consisting of a scintillator inside a Faraday cage, while the BSE detector 15 may be a solid-state detector. The SE detector may be positively charged to attract SEs.

A source 2 of charged particles is configured to emit a beam of charged particles. For example, an electron gun 2 may be configured to emit an electron beam irradiating the sample or the workpiece placed on the sample table 9t. There are three mechanisms of generating the electrons in a SEM: (1) Field emission gun generates a powerful electric field, which pulls electrons away from their atoms and generates high resolution images. (2) Thermionic filament uses tungsten that heats up at white hot temperatures, until it emits electrons. (3) Cerium hexaboride cathode has ten times the brightness of tungsten. Such electron source provides an improved signal-to-noise ratio and has a much longer lifetime.

The sample stage system may include sample stage(s) 9s (which may include any suitable known X-stage and Y-stage) is/are employed to support the sample table 9t and also to move the sample table 9t around on an X-Y plane. A plasma generator 21 is placed in a space between the sample table 9t and the sample stage 9s (e.g. the upper stage as shown in FIG. 1, either X stage or Y stage). The plasma generator 21 may sit onto, or be partially embedded into, the upper sample stage 9s. The sample table 9t has one or more openings or holes 90. The sample table 9t and the plasma generator 21 are so configured that the plasma generator 21 generates an amount of plasma and distributes or dissipates the plasma through the one or more openings 90 of the sample table 9t and toward/onto surface of the BSE detector 15, so as to clean the contaminants thereon.

Figure 2:
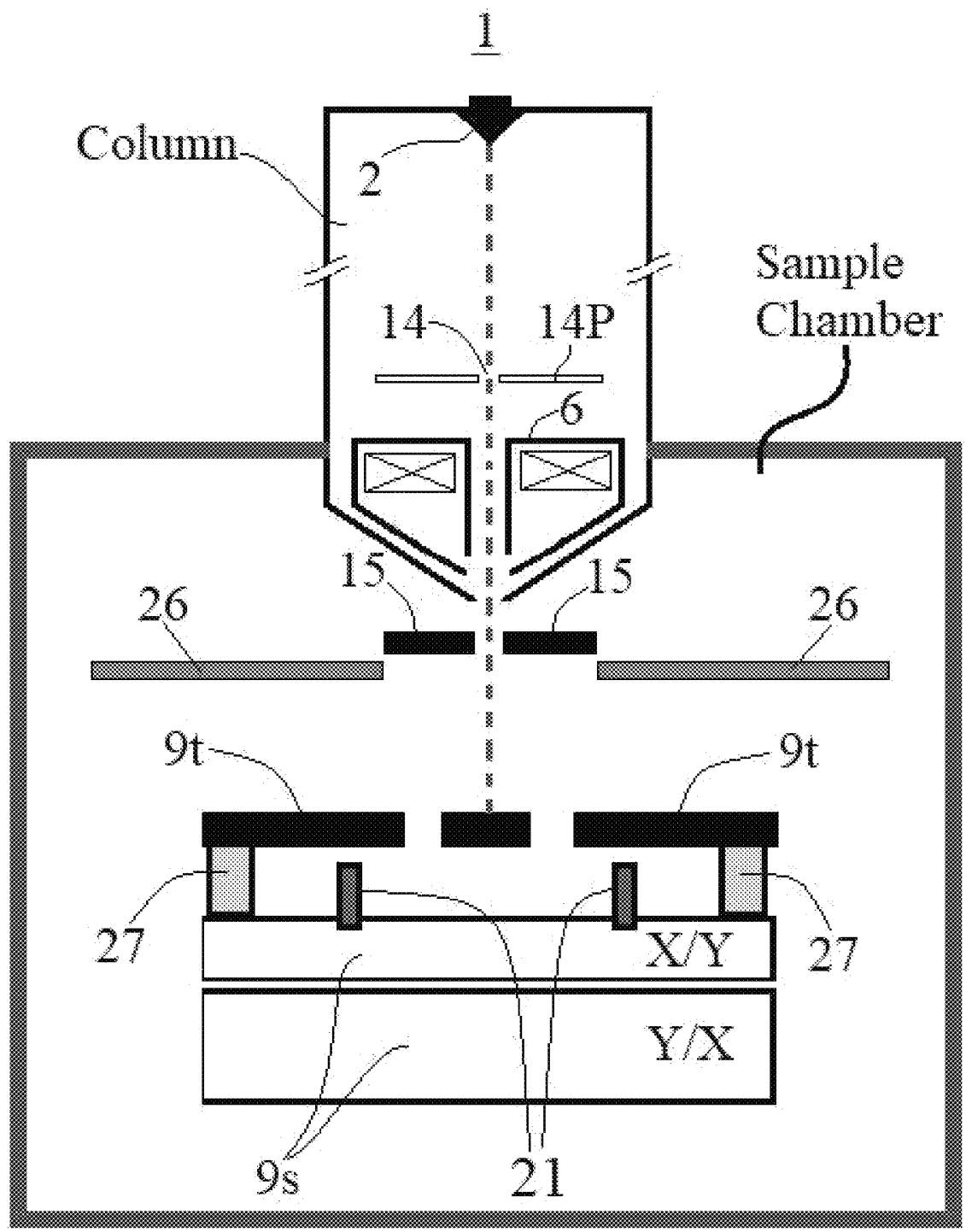
FIG. 2 schematically illustrates a more specific apparatus of charged-particle beam comprising a plasma generator in accordance with an exemplary embodiment of the present invention.

As shown in FIG. 2, the apparatus 1 may further include an objective lens 6 within a column above the BSE detector 15 within a sample chamber. A device 14P of limiting aperture with aperture 14 may be located above the objective lens 6. In preferred embodiments, the plasma from generator 21 is distributed or dissipated on surface of the BSE detector 15 in a concentration higher than that on surface of the device 14 of limiting aperture.

The plasma generator 21 in FIGS. 1-2 may be configured to periodically generate and distribute the plasma for selectively cleaning contaminants on the surface of the BSE detector 15. The BSE detector 15 may have a voltage of 10-25V (e.g. negative voltage) to attract the plasma onto, or concentrate the plasma near, its surface for more efficient and selective plasma cleaning. In some embodiments, a retarding field is generated between a titanium plate 26 and the sample table 9t. The sample stage 9s may be grounded, and ceramic isolators 27 may be used to electrically separate/insulate the sample table 9t from the sample stage 9s.

In various embodiments of the invention, the plasmas are made up of gas atoms in which some or all of the electrons have been stripped away (ionization) and positively charged nuclei (ions) roam freely or not, e.g. under the influence of an electric field (if any). Additionally, moving charged particles generate electric currents, and any movement of a charged plasma particle affects and is affected by the fields created by the other charges. In turn this governs collective behavior with many degrees of variation. The plasma used in the present invention may be nearly fully ionized (i.e. "hot") or partially ionized (i.e. "cold"), where only a small fraction (e.g. 1%) of the gas molecules are ionized. The gas material transforms from being an insulator into a conductor, as it becomes increasingly ionized.

In preferred embodiments, the plasma generator 21 is configured to periodically generate and distribute the plasma for selectively cleaning contaminants on the surface of the BSE detector 15. Plasma cleaning in the invention is a process of removing some or all organic matter from the surface of the detectors through chemical reaction or physical ablation of e.g. hydrocarbons, to form gaseous products. If desired, the gaseous products may be swept away by a continuous gas flow. Sometimes, this may be performed in a vacuum chamber utilizing oxygen and/or argon gas. The cleaning process of the invention is an environmentally safe process as there are no harsh chemicals involved.

In some embodiments, the BSE detector 15 may have a voltage of 10-25V (e.g. a negative voltage) to attract and concentrate the plasma onto their surfaces for more efficient and selective cleaning.

Figure 3:
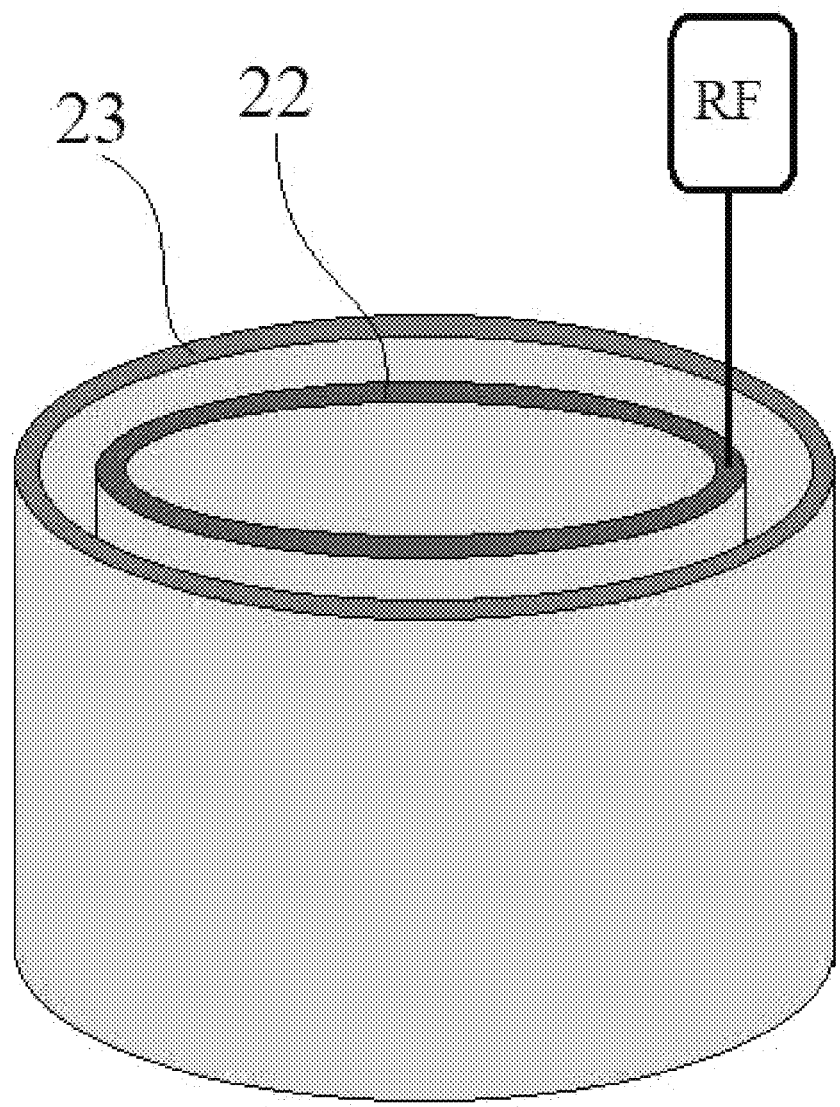
FIG. 3 schematically illustrates a plasma generator having a hollow cylindrical electrode in accordance with an exemplary embodiment of the present invention.

In preferred embodiments as shown in FIG. 3, the plasma generator 21 comprises a source of radio-frequency electrical power (RF), a hollow cylindrical electrode 22 formed of conducting material, and a grounded shield 23 surrounding and enclosing the cylindrical electrode 22 and electrically insulated therefrom. The cylindrical electrode 22 is in communication with the source of radio-frequency electrical power (RF). Upon energizing the electrode 22 with a radio-frequency electric power, a plasma is generated from gas in an interior of the cylindrical electrode 22.

Figure 4:
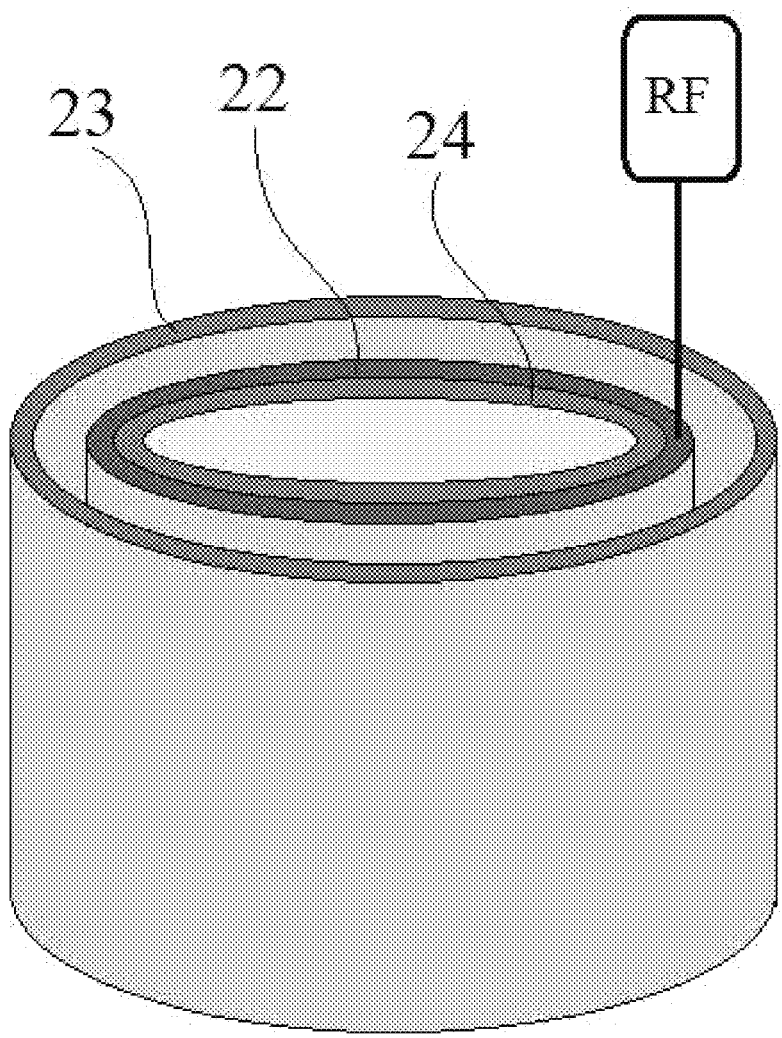
FIG. 4 schematically illustrates a plasma generator having a hollow cylindrical electrode around a dielectric cylinder in accordance with an exemplary embodiment of the present invention.

In other preferred embodiments as shown in FIG. 4, the plasma generator 21 further comprises a hollow dielectric cylinder 24 formed of a dielectric material. The cylindrical electrode 22 may be a brass cylinder around an exterior diameter of the dielectric cylinder 24. The cylindrical electrode 22 is surrounding an exterior of the dielectric cylinder 24. Upon energizing the cylindrical electrode 22 with radio-frequency electric power, a plasma is generated from gas in an interior of the dielectric cylinder 24 by radio-frequency, hollow cathode effect coupling inside the dielectric cylinder 24.

In some exemplary embodiments, the dielectric cylinder 24 is formed of ceramic, glass, quartz, and Teflon such as machinable ceramic comprising about 55% fluorophlogopite mica and 45% borosilicate glass. Without being bound by any particular theory, a virtual anode may be formed by the hollow cathode effect along a central axis of the dielectric cylinder 24 in the plasma and a ground may be defined by the BSE detector 15.

In the apparatus 1 of the present invention, a source of gas may be provided for producing the plasma. For example, a vacuum chamber may be controlled to lower its vacuum pressure, allowing a desired amount of ambient air to flow into the chamber and then the air is used for generating plasma. Alternatively, a source of gas (e.g. a tank) may be in fluid communication with the interior of the cylindrical electrode 22 as shown FIG. 3, or the interior of the dielectric cylinder 24 as shown FIG. 4, through a gas flow control device.

It should be appreciated that any other suitable plasma generator(s) may be employed in the present invention for generating the plasma for cleaning detectors. The type of power source used to generate the plasma of the invention may be DC, AC (typically with radio frequency, but not necessarily limited thereto) and microwave. The plasma may be generated by the application of an electric field, a magnetic field, a microwave, or any combination thereof through a gas selected from oxygen, nitrogen, air, hydrogen, argon, helium, and neon. The pressure for plasma operation may be vacuum pressure (<10 mTorr or 1 Pa), low or moderate pressure (<1 Torr or 100 Pa), or atmospheric pressure (< or =760 Torr or 100 kPa), preferably low or moderate pressure. The desired pressure of a sample chamber may be achieved by controlling a vacuum pump's speed for vacuuming the sample chamber and/or controlling the flow rate of a gas injecting into the sample chamber. The temperature relationships within the plasma may be thermal plasma, non-thermal or cold plasma.

Any known mechanism(s) may be employed in the present invention for generating the plasma. Examples of low-pressure plasma discharge include glow discharge, capacitively coupled plasma (CCP), cascaded arc discharge, inductively coupled plasma (ICP), and wave heated plasma, among others. Glow discharge plasma is non-thermal plasmas generated by the application of DC or low frequency RF (<100 kHz) electric field to the gap between two metal electrodes. Capacitively coupled plasma (CCP) is similar to glow discharge plasmas, but it is generated with high frequency RF electric fields, typically 13.56 MHz. Any known CCP devices used in the microfabrication and integrated circuit manufacturing industries for plasma etching and plasma enhanced chemical vapor deposition may be properly modified and used in the present invention. Cascaded arc plasma source is a device to produce low temperature (≈1 eV) high density plasmas (HDP), and it may also be properly modified and used in the present invention. Inductively coupled plasma (ICP) is similar to CCP except that the electrode consists of a coil wrapped around a chamber where plasma is formed. Wave heated plasma is similar to CCP and ICP in that it is typically RF (or microwave). Examples include helicon discharge and electron cyclotron resonance (ECR), and magnetically induced plasmas (MIP) which is typically produced using microwaves as a resonant coupling method.

Figure 5:
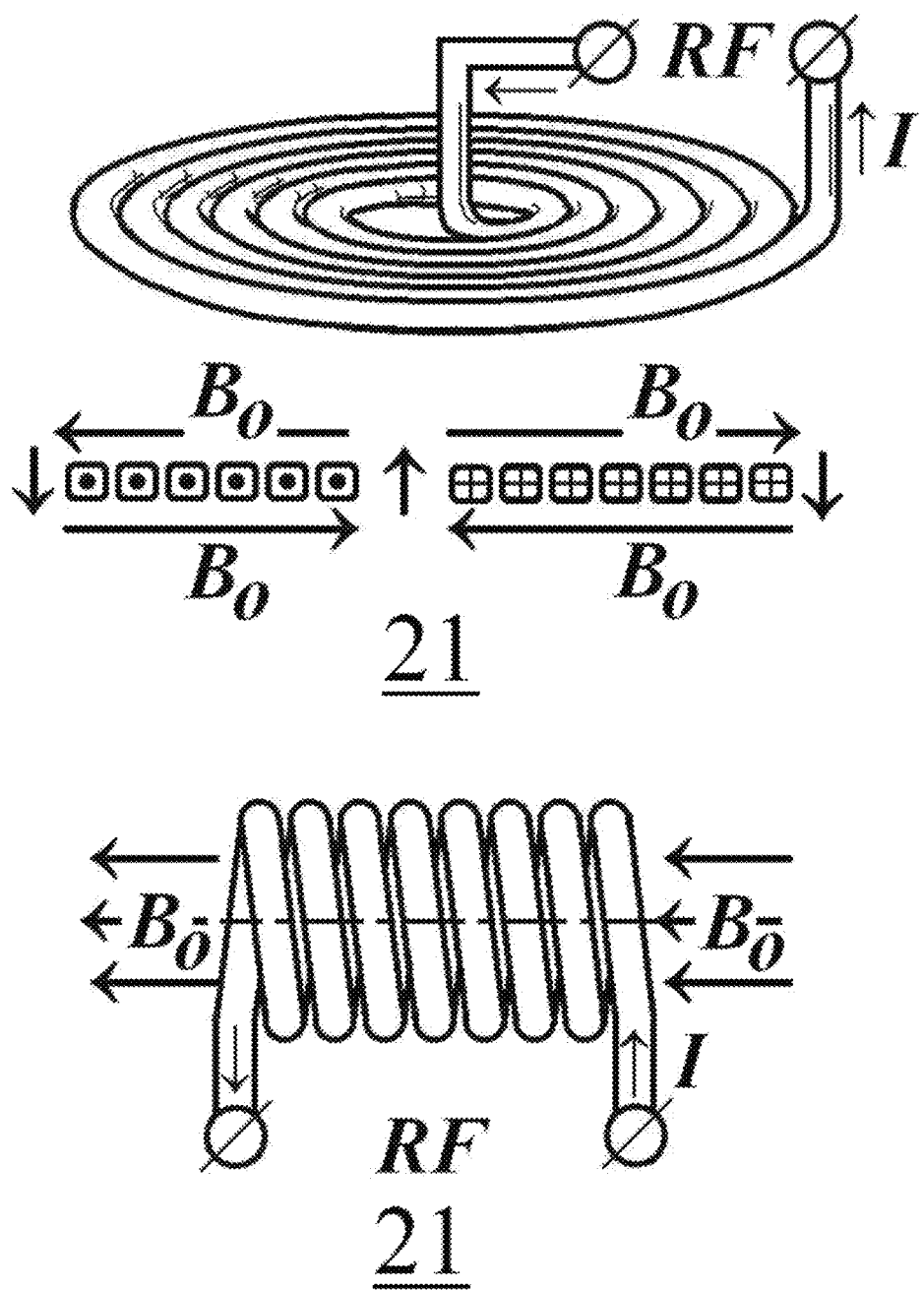
FIG. 5 schematically illustrates some plasma generators useful in the apparatus of charged-particle beam in accordance with an exemplary embodiment of the present invention.
Figure 6:
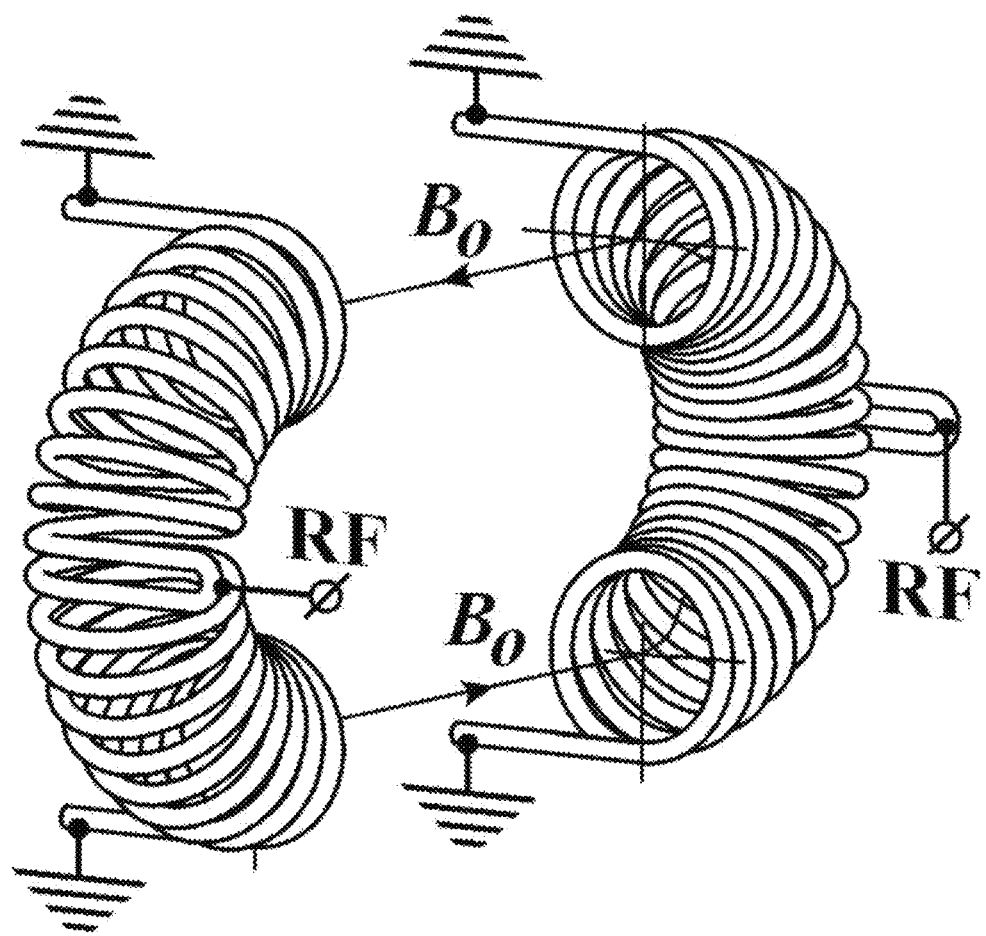
FIG. 6 schematically illustrates another plasma generator useful in the apparatus of charged-particle beam in accordance with an exemplary embodiment of the present invention.

For example, an inductively coupled plasma (ICP) or transformer coupled plasma (TCP) as shown in FIGS. 5-6 may be used in the present invention. The energy is supplied by electric currents which are produced by electromagnetic induction (time-varying magnetic fields). FIG. 5 shows a planar ICP geometry in which the electrode is a length of flat metal wound like a spiral (or coil), and a cylindrical ICP geometry in which it is like a helical spring. FIG. 6 shows a half-toroidal ICP geometry, in which the electrode is toroidal solenoid cut along its main diameter to two equal halves. When a time-varying electric current is passed through the coil, the ICP creates a time-varying magnetic field around it. According to the Faraday-Lenz's law of induction, this creates azimuthal electromotive force in the rarefied gas to generate the plasma. In an embodiment, the ICP uses a radio-frequency-powered (RF) solenoid magnetic field to trap the electrons in the plasma. Because the ICP coil is grounded on one leg, it has low impedance and high current with high heating. The electron energy spread expands due to colliding and circling electrons in the magnetic field without encounters with the sheath. A solenoid coil can be wrapped around a glass or quartz cylinder and excited with RF power to create an inductively coupled plasma (ICP) without the electrode contacting the plasma. The ICP creates a magnetic field within the chamber that traps the free electrons within the coil while they oscillate.

Referring back to FIGS. 3-4, the RF plasma source 21 can be used to create ions, electrons, excited metastables, and atomic radicals depending on choices of gas, pressure, flow rates, RF power and frequency, and extraction electrodes. In certain embodiments, the gas may be air and the BSE detector 15 is cleaned by oxygen radicals that remove carbon compounds by oxidation. In other embodiments, the gas may be hydrogen. As a secondary benefit, RF plasma source 21 can also be used to clean other contaminations on other parts of the apparatus 1 of charged-particle beam, such as pump oils, fingerprints, dirty specimens, and improper vacuum practices in manufacturing and operation. Plasma cleaning with an air plasma removes hydrocarbons with a chemical etch where the oxygen in air is disassociated into neutral O radicals (atoms) or metastables. These species react quickly with hydrocarbons to produce $H_2O$, $CO_2$, CO, $H_2CO$, and other short chain volatile hydrocarbons that can be removed by the vacuum pumps. Hydrogen gas can also be used in a plasma for cleaning by reduction of the hydrocarbons. Other frequently used gases include combinations of $N_2$, $O_2$, $H_2$, fluorocarbons, as well as inert diluent gasses He, Ne, Ar, Ne, and Xe.

The radio-frequency-excited hollow cathode (RF-HC) 22 may become a plasma radical source and it can create an excited gas plasma inside the apparatus 1 of charged-particle beam, such as a vacuum chamber in an electron microscope. The hollow cathode 22 may be made from an aluminum screen by machining or from punched sheet metal. Electrode 22 may also be "assembled" of halves or quarters machined or otherwise formed from electrically conductive metals or other conductive materials that are closely joined together, electrically, physically, or structurally, upon assembly. Electrode 22 may be a continuous thin conductive cylinder, as distinguished from a coil or other interrupted structure, to avoid inductive coupling effects. Other conductive materials such as aluminum or copper could also be used for the electrode. A cylindrical, electrically conductive shield 23 may be placed around the electrode 22 and is electrically grounded. Shield 23 may be grounded by a connection to the shield of a RF cable (not shown). An insulator in the form of an air gap (as shown), or solid dielectric material (not shown), may be used to separate electrode 22 from shield 23.

In an embodiment, an aluminum cylindrical hollow cathode 22 as shown in FIG. 3 is immersed in the plasma during operation. At low power (<20 Watts RF @13.56 MHz) this may work well and is particularly preferred. However, at a higher power, overheating and electrode erosion occurred and discoloration formed on the interior walls of the plasma source as shown in FIG. 3. This may suggest material losses from the electrode 22 and its support structure. The RF power may be fed through a power feedthrough on a flange (not shown) which supports the electrode 22 on its axis via a support cross bar (not shown).

In other embodiments, the plasma generator 21 as shown in FIG. 4 is more preferred, since the design enables low voltage, high current operation to prevent overheating, erosion of the electrode, and particulate generation. Due to the dielectric cylinder, this design removes the conductive material of the electrode 22 from contacting with ions from the plasma. The plasma chamber and electrode 22 can be mounted inside an outer grounded shell 23 for electrical safety. The reactant gas may be air because it is a convenient source of oxygen. Other oxygen gas mixtures and pure oxygen can be used or reducing gas can be used. These mixtures can contain hydrogen, water vapor, He, Ar, Ne, F and compounds thereof. For cleaning by reduction H2 and ammonia could be used. With an exterior hollow cathode 22, the dielectric cylinder 24 will partially enclose and define a plasma sheath. Ions will create secondary electrons when they collide with the dielectric material and the expelled ions will be accelerated into the plasma by the sheath. Inside the plasma the high energy ions are very effective in ionization and disassociation of the gas molecules.

Although atmospheric pressure plasma can be used in the present invention, it is less preferred. Examples include arc discharge, corona discharge, dielectric barrier discharge (DBD), capacitive discharge, and piezoelectric direct discharge plasma. Corona discharge is a non-thermal discharge generated by the application of high voltage to sharp electrode tips. Dielectric barrier discharge (DBD) is a nonthermal discharge generated by the application of high voltages across small gaps wherein a non-conducting coating prevents the transition of the plasma discharge into an arc. Capacitive discharge is a nonthermal plasma generated by the application of RF power (e.g., 13.56 MHz) to one powered electrode, with a grounded electrode held at a small separation distance on the order of 1 cm. Such discharges are commonly stabilized using a noble gas such as helium or argon. Piezoelectric direct discharge plasma is a nonthermal plasma generated at the high-side of a piezoelectric transformer (PT).

Figure 7:
FIG. 7 is a flow chart showing a method of selectively cleaning BSE detector in an apparatus of charged-particle beam in accordance with an exemplary embodiment of the present invention.

Another aspect of the present invention provides a method of selectively cleaning BSE detector 15 in an apparatus 1 of charged-particle beam, as shown in FIG. 7. The method includes a step of installing a plasma generator 21 within the apparatus 1 in a manner as described above; and another step of generating plasma to selectively clean the BSE detector 15.

Figure 17:
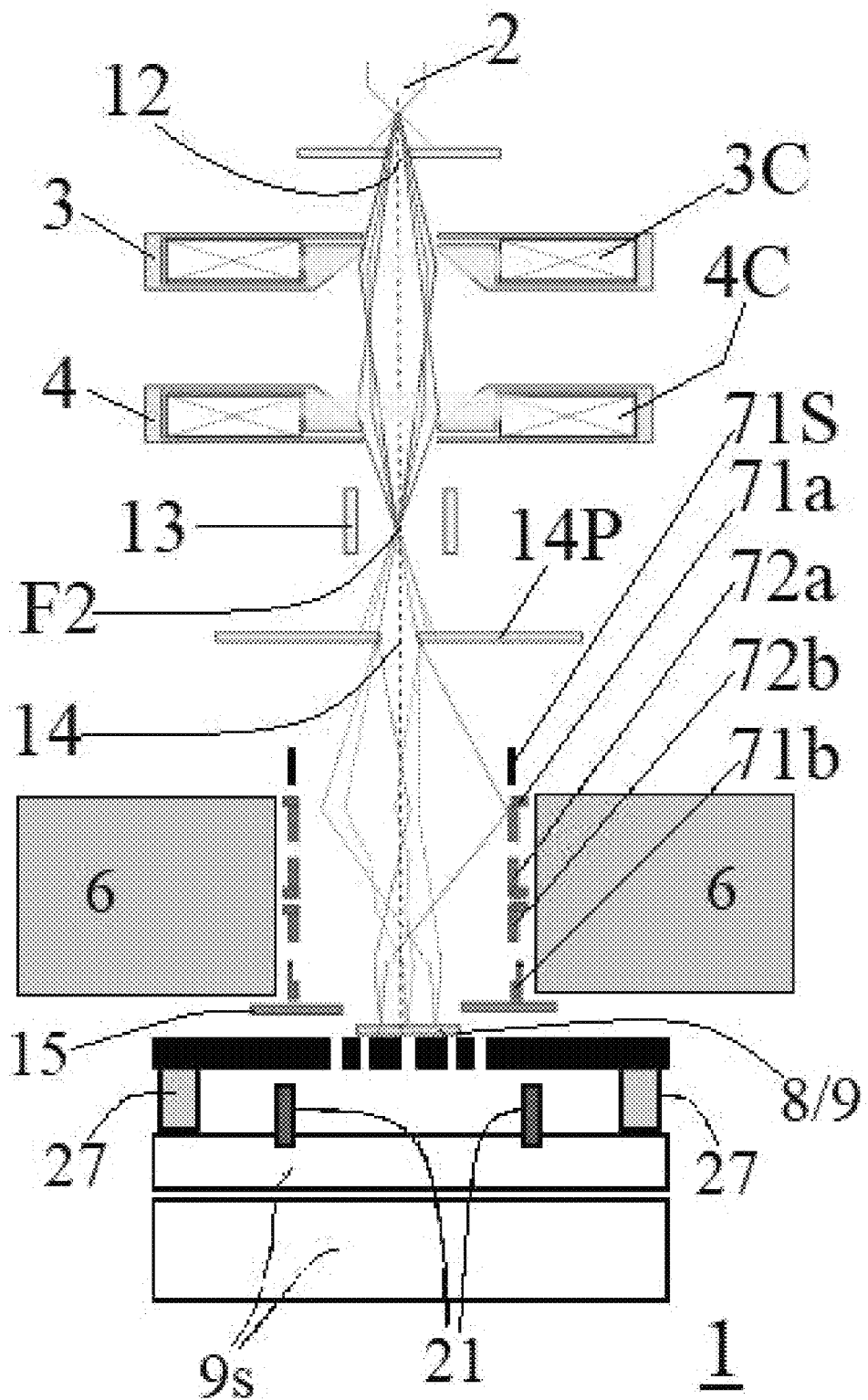
FIG. 17 shows a specific apparatus of charged-particle beam with the plasma generator in accordance with an exemplary embodiment of the present invention.

In some embodiments, the apparatus of charged-particle beam 1 may include a charged-particle optical column and a sample chamber as shown in FIG. 2. For example, the charged-particle optical column may include one or more charged-particle optical components along the beam path, selected from a source of charged particles configured to emit a beam of charged particles such as an electron gun 2 configured to emit an electron beam, condenser(s), stigmator(s), alignment coil(s), alignment plate(s), beam blanking(s), plate(s) 14P with objective (or limiting) aperture(s) 14, plate(s) with spread aperture(s), deflector(s), magnetic objective lens(es), and detector(s). The sample chamber may include one or more chamber components selected from a specimen holder 9 for holding a specimen under examination, a receptacle for receiving a lithographical workpiece (e.g. mask or wafer) being processed with the beam, and one or more detectors for detecting charged particles (such as BSE detector 15). As shown in FIG. 17, charged-particle optical components within the column may be electron optical components selected from the following (from upstream to downstream): an electron gun 2 configured to emit an electron beam, a first co-condenser 3, a second co-condenser 4, a beam blanking 13, a plate 14P with an objective aperture 14, a stigmator 71s, an upper macroscopic deflector 71a, an upper microscopic deflector 72a, a lower microscopic deflector 72b, a lower macroscopic deflector 71b, a magnetic objective lens 6, and a BSE or SE detector 15.

In preferred embodiments, the apparatus of charged-particle beam 1 is an electron microscope (such as SEM), or an electron beam lithography apparatus. In the following exemplary embodiments, the plasma generator 21 of the invention is used to optimize an apparatus of charged-particle beam 1 having con-condensers as shown in FIGS. 8-9.

In an apparatus 1 of charged-particle beam such as an electron microscope (e.g. SEM), the manipulation of an electron beam is performed using two physical effects. The interaction of electrons with a magnetic field will cause electrons to move according to the left-hand rule, thus allowing for electromagnets to manipulate the electron beam. The use of magnetic fields allows for the formation of a magnetic lens of variable focusing power, and the lens shape is determined by the distribution of magnetic flux. Electrostatic fields can cause the electrons to be deflected through a constant angle. Coupling of two deflections in opposing directions with a small intermediate gap allows for the formation of a shift in the beam path. From these two effects, as well as the use of an electron imaging system, sufficient control over the beam path is made possible. The lenses in the beam path can be enabled, tuned, and disabled entirely and simply via rapid electrical switching, the speed of which is only limited by effects such as the magnetic hysteresis.

Figure 8:
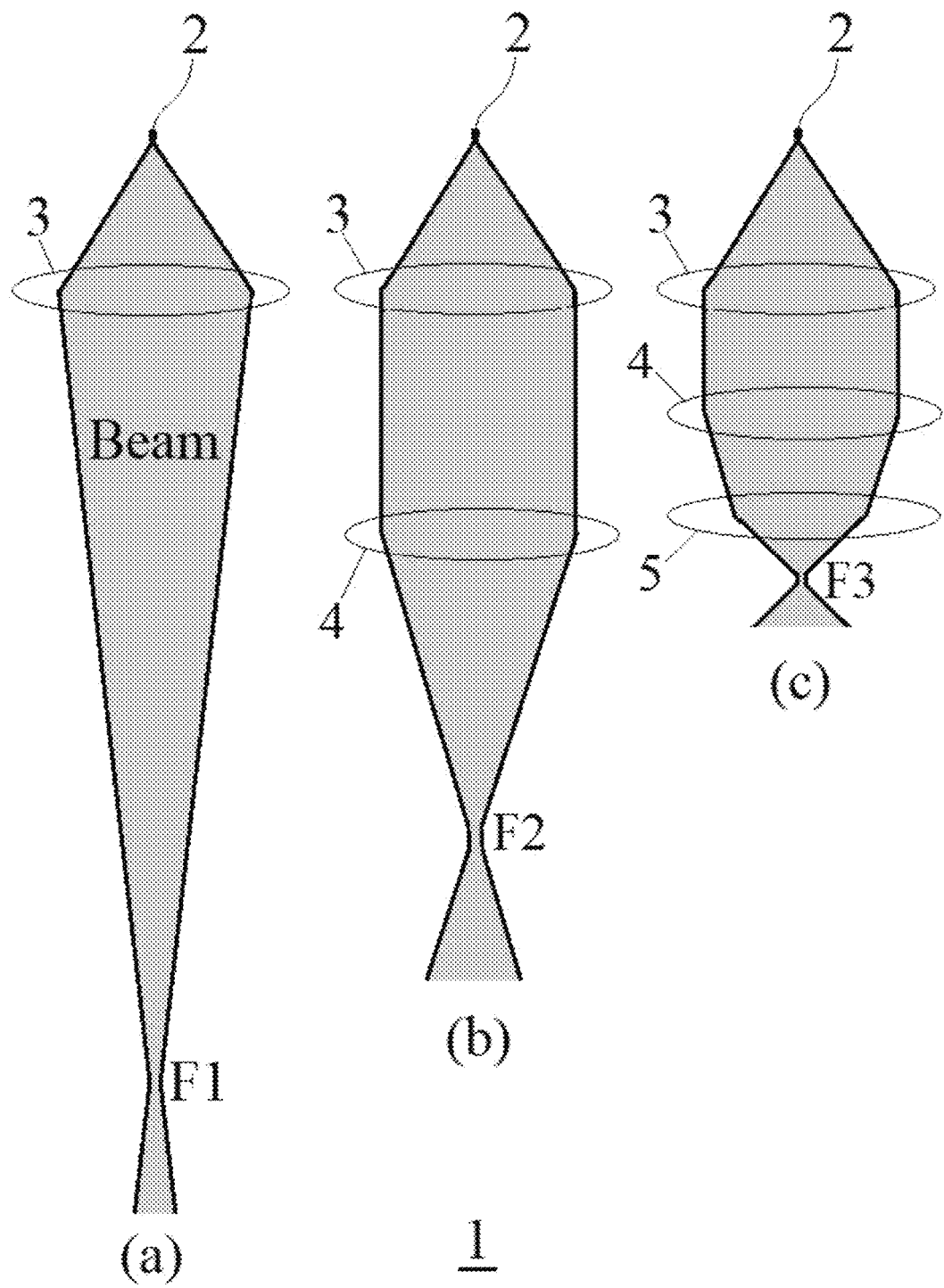
FIG. 8 schematically illustrates the formation of co-condensers which can be used in an apparatus of charged-particle beam with a plasma generator in accordance with an exemplary embodiment of the present invention.
Figure 9:
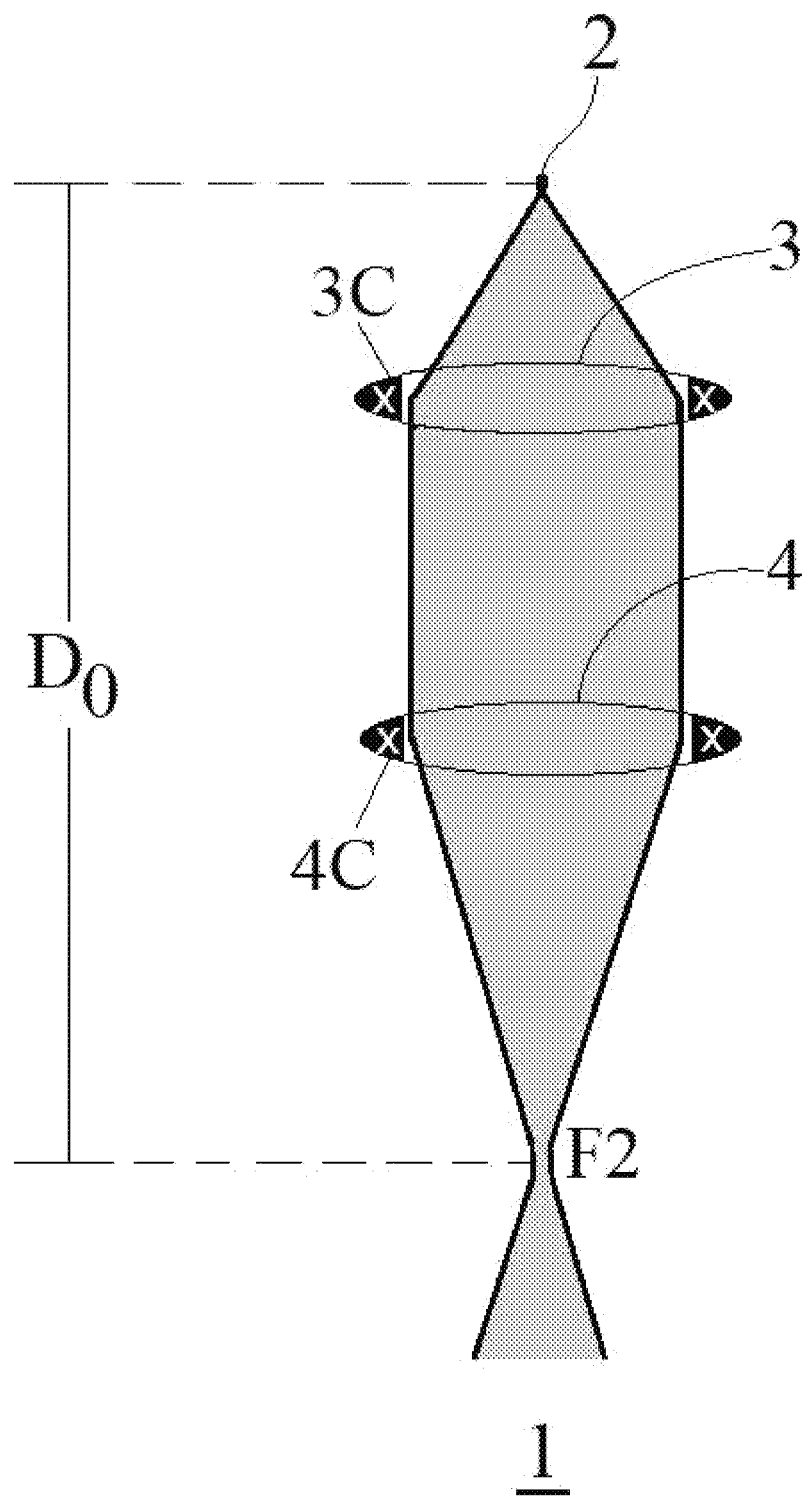
FIG. 9 shows two co-condensers with magnetic coils which can be used in an apparatus of charged-particle beam with a plasma generator in accordance with an exemplary embodiment of the present invention.

In an apparatus 1 of charged-particle beam as shown in FIG. 8, a source 2 of charged particles is configured to emit a beam of charged particles. The source 2 may be for example an electron gun with a tungsten filament or a lanthanum hexaboride ($LaB_6$). In panel (a), a magnetic condenser 3 alone can focus the beam to a crossover spot F1. The beam is expanded after a crossover spot. In panel (b), another magnetic condenser 4 is placed between magnetic condenser 3 and crossover spot F1, and the beam is now focused to a new crossover spot F2 that is closer to source 2 than spot F1. In panel (c), a third magnetic condenser 5 is placed between magnetic condenser 4 and crossover spot F2, and the beam is again focused to another new crossover spot F3 that is even closer to source 2 than spot F2.

Generally, a condenser lens forms an image of the primary electron beam source for an objective lens, and the objective lens focuses the condenser lens image onto a specimen or a workpiece. Transmitted, secondary and backscattered electrons are released from the specimen material. These electrons are detected, amplified and the resulting signal used to modulate the beam of an imaging system operating synchronously with the scanning electron beam. The result is an image of the scanned area based on the electrons emitted or scattered from the specimen.

In the present invention, the term "co-condensers" is defined as two or more magnetic condensers configured to coherently focus the beam to a single crossover spot F. For example, magnetic condensers 3 and 4 in panel (b) coherently focus the beam to a single crossover spot F2, and they may be called a set of co-condensers. Magnetic condensers 3, 4 and 5 in panel (c) coherently focus the beam to a single crossover spot F3, and they may also be called a set of co-condensers. As shown in FIG. 8, the beam does not have any crossover spot between any two of the two or more magnetic condensers within a set of co-condensers.

The crossover spot F may be movable or immovable. In some embodiments of the invention, the single crossover spot F is so controlled that it remains stationary or immovable relative to the source 2 of charged particles. For example, crossover spot F2 may be kept stationary relative to the source 2, i.e. the distance D0 between spot F2 and source 2 remains unchanged. By the same token, crossover spot F3 may be kept stationary relative to the source 2, i.e. the distance D0 between spot F3 and source 2 remains unchanged.

While the single crossover spot F remains immovable relative to the source 2 of charged particles, the size A of the beam at crossover spot F (i.e. the cross-sectional area of the beam at F) may be so controlled to have a desired value. Preferably, size A may be tuned/adjusted by concertedly tuning/adjusting the individual condensing capacity of the two or more magnetic condensers within a set of co-condensers. For example, the condensing capacity of condenser 3 and that of condenser 4 may be individually but concertedly tuned/adjusted so that not only the single crossover spot F2 is fixed relative to the source 2, but also the size A of the beam at crossover spot F2 is controlled to have a value as desired. Likewise, the condensing capacities of two or more condensers 3, 4 and 5 may be individually but concertedly tuned/adjusted so that not only the single crossover spot F3 is fixed relative to the source 2, but also the size A of the beam at crossover spot F3 is controlled to have a value as desired. The two or more co-condensers are therefore configured to coherently focus the beam to the same cross-over point with different magnification rates.

Although the apparatus 1 may include one, two or more sets of co-condensers, in some preferred embodiments of the invention, the apparatus 1 includes only one set of co-condensers with only two magnetic condensers configured to coherently focus the beam to a single crossover spot F. For example, the apparatus 1 may include only one set of co-condensers as shown in Panel (b) of FIG. 8 with only two magnetic condensers (3, 4) configured to coherently focus the beam to a single crossover spot F2.

Referring now to FIG. 9, the only two magnetic condensers (3, 4) include a distal magnetic condenser 4 which is distal to the source 2, and a proximal magnetic condenser 3 that is located between the source 2 and the distal magnetic condenser 4. The proximal magnetic condenser 3 comprises a magnetic coil 3C driven by a coil current I1; and the distal magnetic condenser 4 comprises a magnetic coil 4C driven by a coil current I2. Generally, both coil currents I1 and I2 are greater than 0 (>0).

In preferred embodiments of the invention, coil currents I1 and I2 are configured to position single crossover spot F2 at a fixed position, i.e. maintain a predetermined distance D0 from source 2. With the "fixed F2" condition being met, the size A of the crossover spot F2 may be increased by increasing coil current I1 and/or decreasing coil current I2; and decreased by decreasing coil current I1 and/or increasing coil current I2. The size A of the crossover spot F2 will be minimized when coil current I1 reaches its minimal value while coil current I2 reaches its maximal value. The size A is maximized when coil current I2 reaches its minimal value while I1 reaches its maximal value. There is no special limitation on the maximized size A, it may be smaller than, equal to, or bigger than the size of the source 2.

Figure 10:
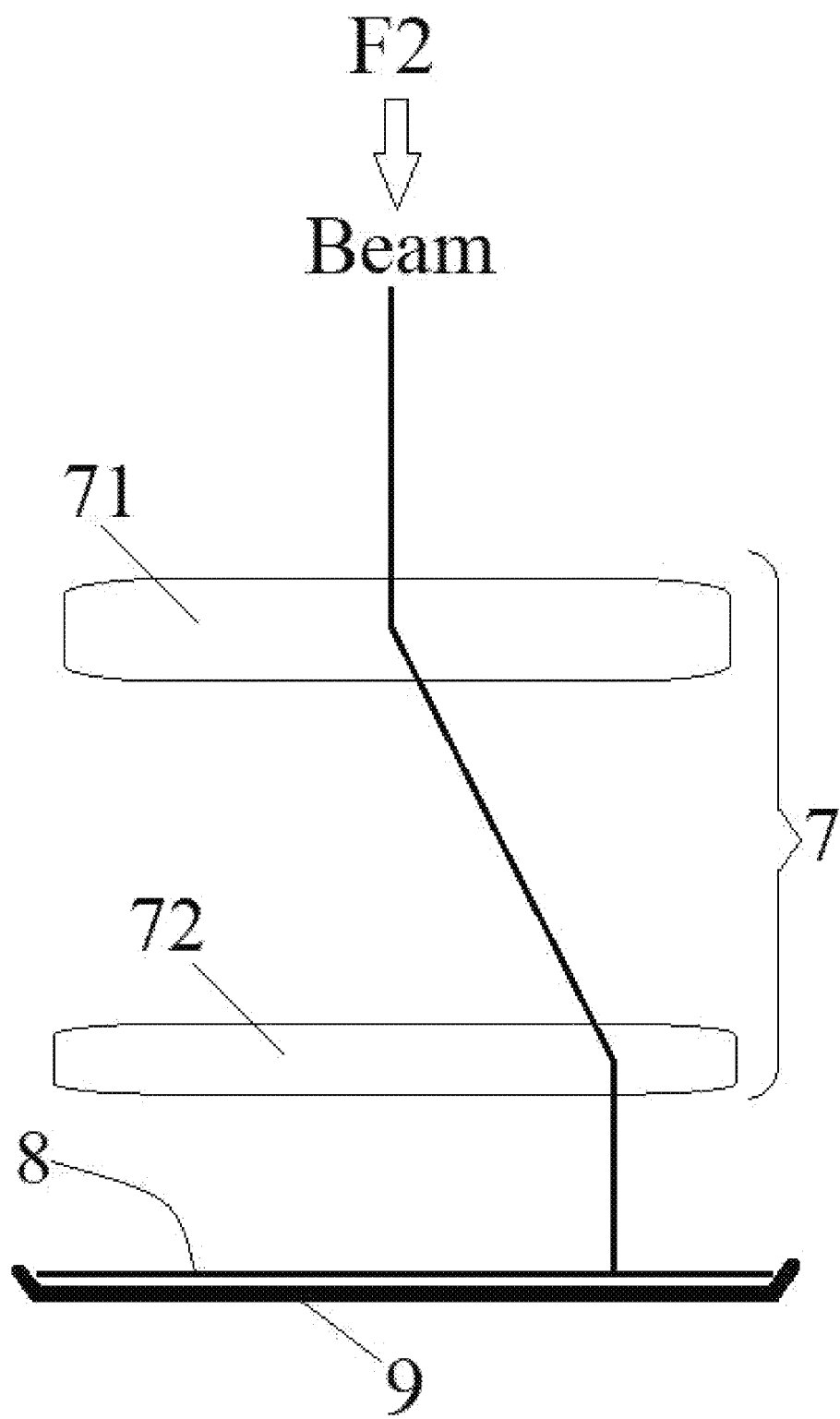
FIG. 10 illustrates an apparatus of charged-particle beam with a magnetic objective lens and a deflection system which can be used with the plasma generator in accordance with an exemplary embodiment of the present invention.
Figure 15:
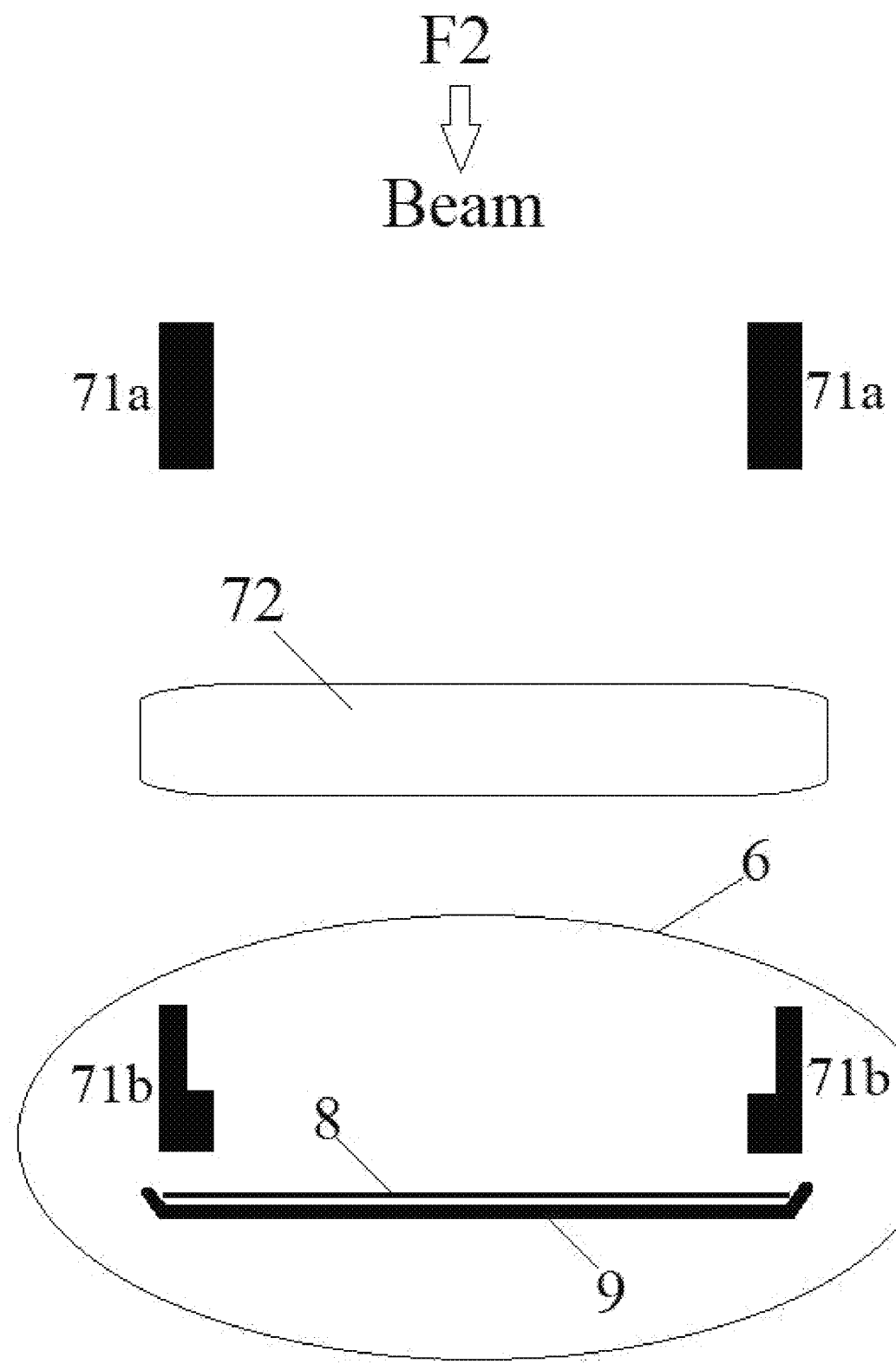
FIG. 15 schematically illustrates the configuration of a macroscopic deflection sub-system which can be used with the plasma generator in accordance with an exemplary embodiment of the present invention.
Figure 16:
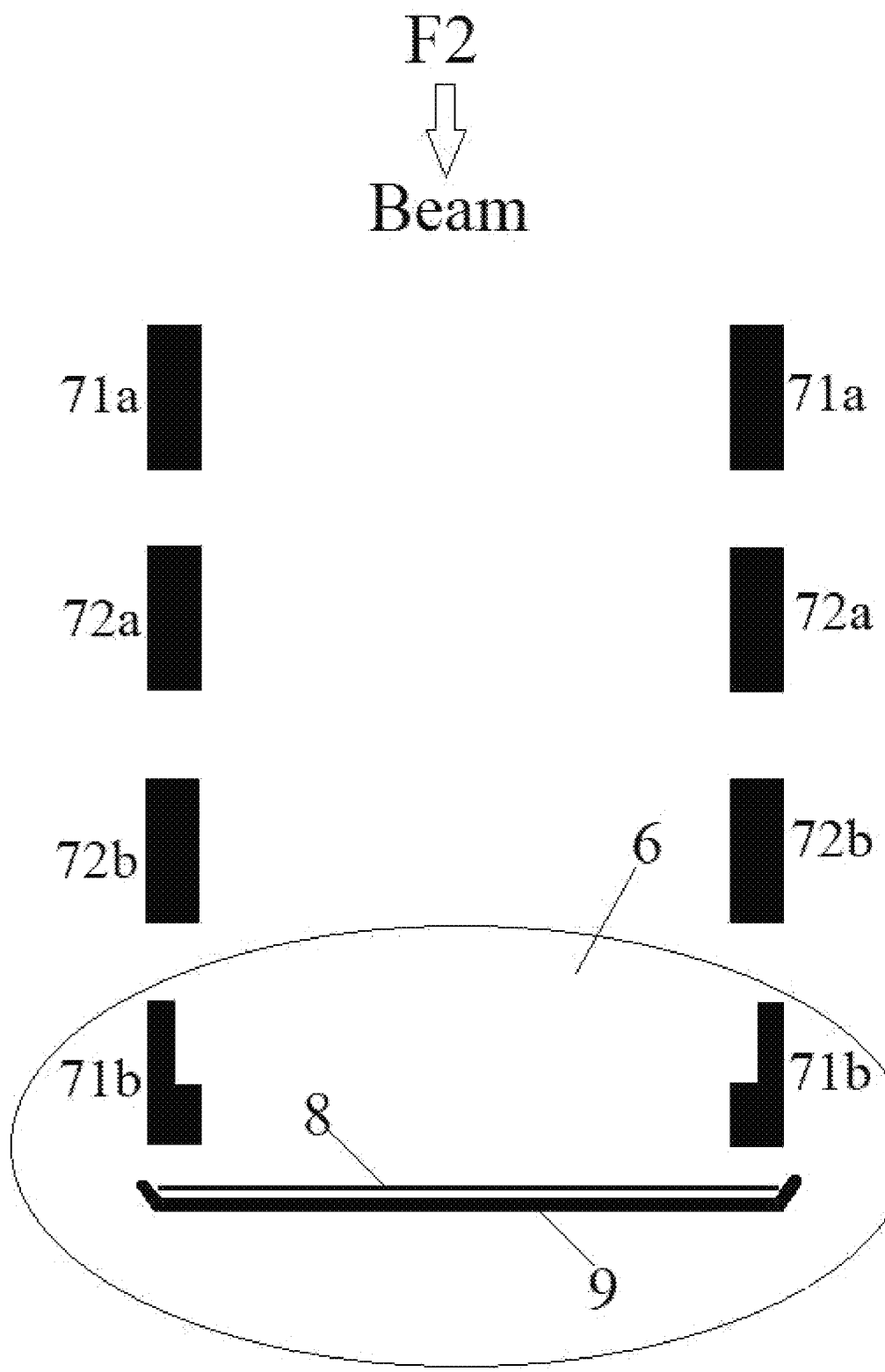
FIG. 16 schematically illustrates the configuration of a microscopic deflection sub-system which can be used with the plasma generator in accordance with an exemplary embodiment of the present invention.

In various exemplary embodiments as shown in FIG. 10, the apparatus of charged-particle beam according to the invention may include a magnetic objective lens 6 (as shown in FIGS. 15-17) and a deflection system 7, both of which are downstream with respect to the single crossover spot F (e.g. F2). Although electron lenses may operate electrostatically or magnetically, most electron lenses use electromagnetic coils to generate a convex lens. The field produced for the lens is typically radially symmetrical, as deviation from the radial symmetry of the magnetic lens causes aberrations such as astigmatism and worsens spherical and chromatic aberration. For example, a quadrupole lens is an arrangement of electromagnetic coils at the vertices of the square, enabling the generation of a lensing magnetic fields, the hexapole configuration simply enhances the lens symmetry by using six, rather than four coils. Electron lenses may be manufactured from iron, iron-cobalt or nickel cobalt alloys, such as permalloy, due to their good magnetic properties, such as magnetic saturation, hysteresis and permeability. It should be appreciated that the objective lens 6 may be an electromagnetic lens or an electrostatic lens.

Objective lens 6 allows for electron beam convergence, with the angle of convergence as a variable parameter. The magnification may be simply changed by modifying the amount of current that flows through the coil of lenses. Lens 6 may include yoke, magnetic coil, poles, pole piece, and external control circuitry. An electromagnetic lens 6 may include an upper pole piece and a lower pole piece. The pole piece must be manufactured in a very symmetrical manner, as this provides the boundary conditions for the magnetic field that forms the lens. Imperfections in the manufacture of the pole piece can induce severe distortions in the magnetic field symmetry, which induce distortions that will ultimately limit the lenses' ability to reproduce the object plane. The exact dimensions of the gap, pole piece internal diameter and taper, as well as the overall design of the lens is often performed by finite element analysis of the magnetic field, taking into account of the thermal and electrical constraints of the design. The coils which produce the magnetic field are located within the lens yoke. The coils can contain a variable current, but typically utilize high voltages, and therefore require significant insulation in order to prevent short-circuiting the lens components. Thermal distributors are placed to ensure the extraction of the heat generated by the energy lost to resistance of the coil windings. The windings may be water-cooled, using a chilled water supply in order to facilitate the removal of the high thermal duty.

A magnetic lens may include a magnetic material and exciting coils for providing magnetomotive force to a magnetic circuit having field lines through the magnetic material and between pole faces.

For the deflection system 7, it may include a macroscopic deflection sub-system 71 and a microscopic deflection sub-system 72. The deflection system 7 causes the beam to position at, and scan across, a large field of view (FOV) on a specimen plane 8 of a specimen under examination in a specimen holder 9 and one or more small FOVs within the large FOV.

Figure 11:
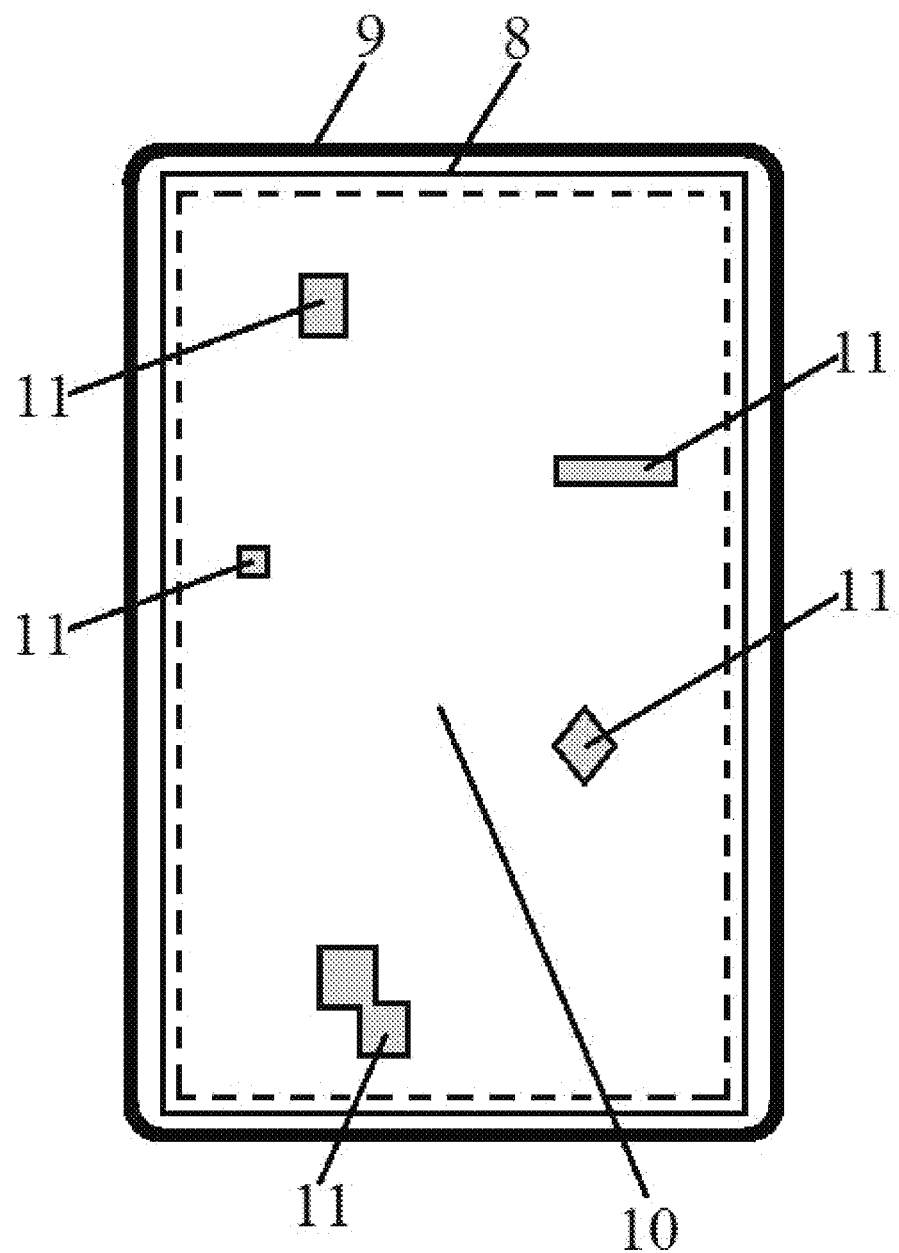
FIG. 11 demonstrates a single large field of view (FOV) on the specimen plane of the apparatus in accordance with an exemplary embodiment of the present invention.
Figure 12:
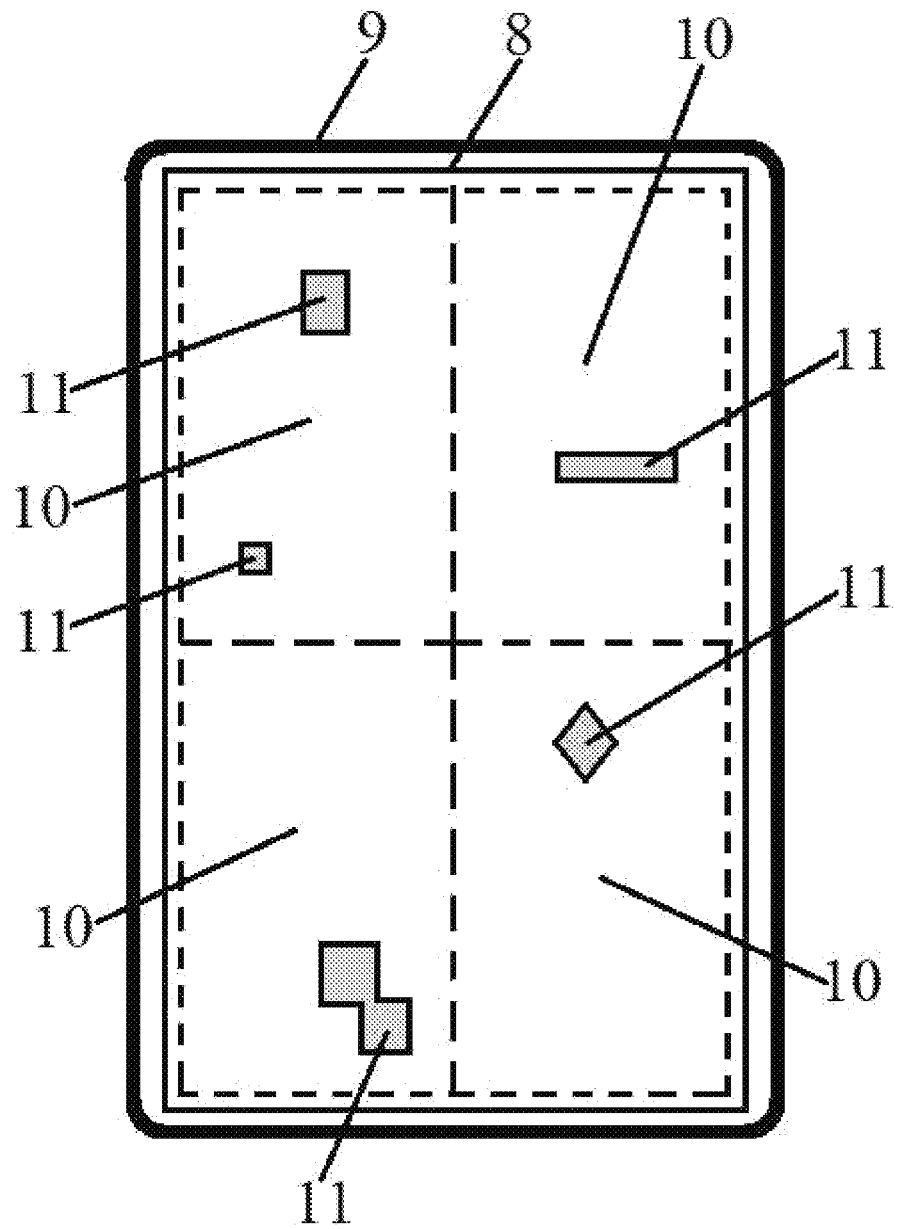
FIG. 12 demonstrates multiple large FOVs on the specimen plane of the apparatus in accordance with an exemplary embodiment of the present invention.

As shown in FIGS. 11 and 12, the macroscopic deflection sub-system 71 causes the beam to scan across a large field of view (FOV) 10 on the specimen plane 8 of the specimen holder 9, and the microscopic sub-deflection system 72 causes the beam to position at, and scan across, one or more small FOVs 11 within a large FOV. As shown in FIG. 11, the specimen plane 8 may contain only one large FOV 10, which may contain zero, one, two, three or more small FOVs 11. In FIG. 12, the specimen plane 8 may contain two, three or more large FOVs 10, each of which may contain zero, one, two, three or more small FOVs 11.

Figure 13:
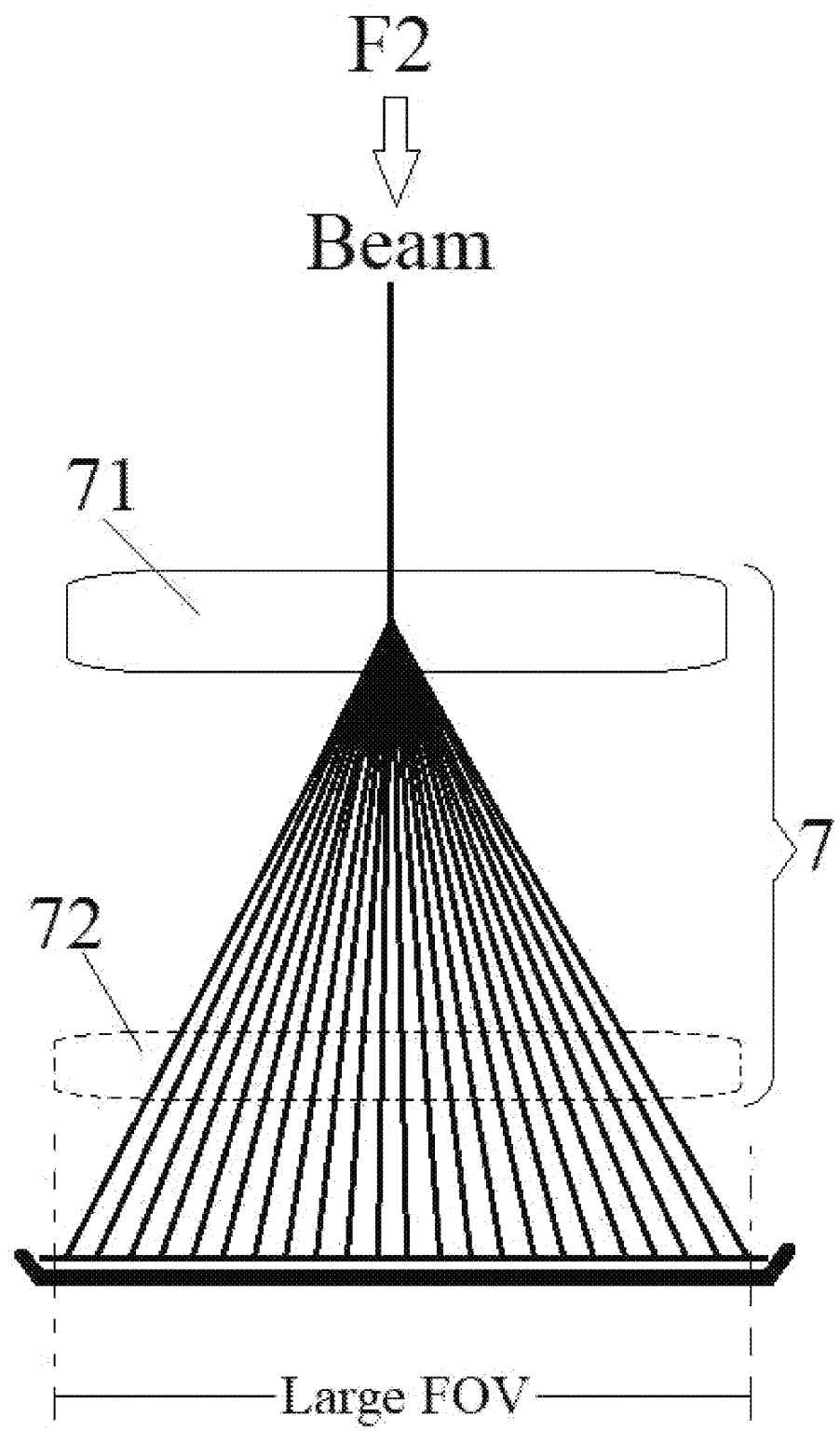
FIG. 13 illustrates a macroscopic deflection sub-system in accordance with an exemplary embodiment of the present invention that alone causes the beam to scan across a large FOV

In the first step of an examination process as shown in FIG. 13, a user may turn off or inactivate the microscopic sub-deflection system 72. Then, the macroscopic deflection sub-system 71 causes the beam to scan across a large FOV 10 on the specimen plane 8 of the specimen holder 9 under a lower resolution (e.g. 10 nm). After the large FOV scanning is completed, the user finds a pattern of interesting (POI) in one or more small FOVs 11 within that large FOV 10, and the user will then zoom into the POI for further examination with a higher resolution (e.g. 1 nm). As an advantage of the present invention, the user will not need to mechanically move the specimen holder 9 to reposition or align the specimen plane 8 to the center of a target small FOV 11. In other words, the specimen holder 9 remains stationary relative to the source 2 of charged particles, no matter the beam is scanning across a given large FOV 10 or subsequently scanning across one, two or more small FOVs 11 within that large FOV 10.

Figure 14:
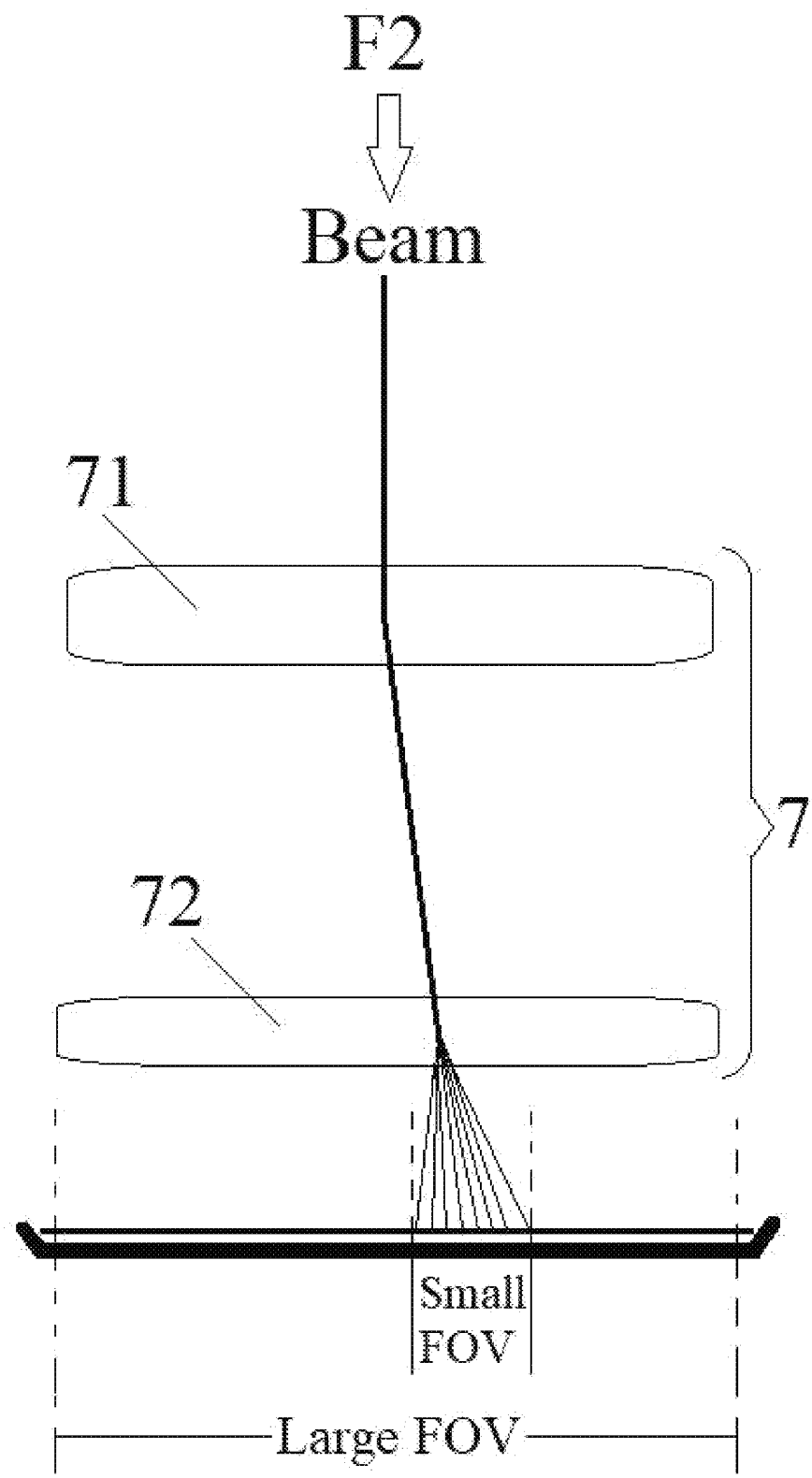
FIG. 14 illustrates a microscopic deflection sub-system causing the beam to scan across a small FOV in accordance with an exemplary embodiment of the present invention.

Instead, the user may run the second step by simply retrieving stored deflecting parameter(s) of the macroscopic deflection sub-system 71 which previously directed the beam to the center of the target small FOV 11. The retrieved deflecting parameter(s) of the macroscopic deflection sub-system 71 will then be re-applied to the subsystem 71, to direct the beam to the center of the target small FOV 11. Generally, the position of any small FOV within a large FOV may be controlled as desired by the macroscopic deflection sub-system 71 by retrieving and re-applying stored deflecting parameters (e.g. voltages). As shown in FIG. 14, after the position of the small FOV within the large FOV is fixed by the macroscopic deflection sub-system 71, the retrieved and re-applied deflecting parameter(s) of the macroscopic deflection sub-system 71 will remain unchanged. Then, the deflecting parameter(s) of the microscopic deflection sub-system 72 is/are varied to cause the beam to scan across the small FOV with a higher resolution.

In various embodiments of the invention, when the beam scans across the large FOV 10 in the first step, the spot F2 has a size A1. When the beam scans across the small FOV 11 within the large FOV 10 in the second step, the spot F2 has a size A2, and A2<A1. The inequation of A2<A1 will result in the resolution for scanning a small FOV is higher than that for a large FOV.

Typically, the size of the large FOV 10 is adjustable, and its image may range from 50 um×50 um to 200 um×200 um in size with a resolution of 0.5-20 nm. For example, the large FOV 10 may have a size of 100 um×100 um with a resolution of 8 nm. The small FOV 11 (e.g. POI, or area of interest) is also adjustable, and it may range from 0.5 um×0.5 um to 5 um×5 um in size with a resolution of 0.5-2 nm. For example, the small FOV may have a size of 5 um×5 um with a resolution of 0.5 nm.

As shown in FIG. 15, the macroscopic deflection subsystem 71 may include an upper deflector 71a, and a lower deflector 71b. The microscopic deflection sub-system 72 may be located between the upper deflector 71a and the lower deflector 71b of the macroscopic deflection system 71. The specimen holder 9 may be downstream with respect to the lower deflector 71b of the macroscopic deflection subsystem 71. As shown in FIG. 16, the microscopic deflection sub-system 72 may also include an upper deflector 72a and a lower deflector 72b.

Any other components known in any apparatus of charged-particle beam, or their proper combination, may be incorporated in the present invention. For a skilled person in the art, many of the components not shown in FIG. 1 or 8 are well-known, for example, suppressor electrode, beam extractor, anode, gun aperture, condenser lens that is responsible for primary beam formation, beam blanker, stigmator for the correction of asymmetrical beam distortions, objective aperture, SEM up detector, deflector, bright field (BF) detector, dark field (DF) detector. A system for the insertion into, motion within, and removal of specimens from the beam path is also needed. The system may include load lock, chamber interlock, lock port, loading and unloading mechanism, and transfer table. Other parts in the microscope may be omitted or merely suggested. In a specific yet exemplary electron microscope 1 as shown in FIG. 17, the source of charged particles may be an electron gun 2 configured to emit an electron beam through gun aperture 12. Along the beam trajectory, co-condenser 3 with magnetic coil 3C is placed between gun aperture 12 and co-condenser 4 with a magnetic coil 4C. The electron beam is focused to crossover spot F2 before it passes through beam blanking 13. After the beam passes through objective aperture 14, it is deflected by an upper deflector 71a and a lower deflector 71b in the macroscopic deflection sub-system 71. It can also be deflected by an upper deflector 72a and a lower deflector 72b in the microscopic deflection sub-system 72. In the meanwhile, the beam is focused by the magnetic objective lens 6 onto a specimen within the specimen holder 9. Electrons scattered from and penetrated through the specimen are detected by the BSE detector 15 for generating specimen images. Deflectors 71a, 72a, 72b and 71b may reside in the central bore the magnetic objective lens 6, and they are disk-shaped rings which are axially symmetric about the Z-axis. Each deflector may have a same or different diameter and may fit at a particular position along the Z-axis. An actual bucket-shaped structure may be used to holds the deflectors, and the structure is inserted into the bucket-shaped space of the lens system thus making assembly easier.

The multiple deflection system (71a, 71b, 72a and 72b) is designed to control electron deflection with different FOV size. For example, deflectors or deflection nodes 71a and 71b control electron beam to be incident on a large FOV, while deflectors 72a and 72b on a small FOV size.

Figure 18:
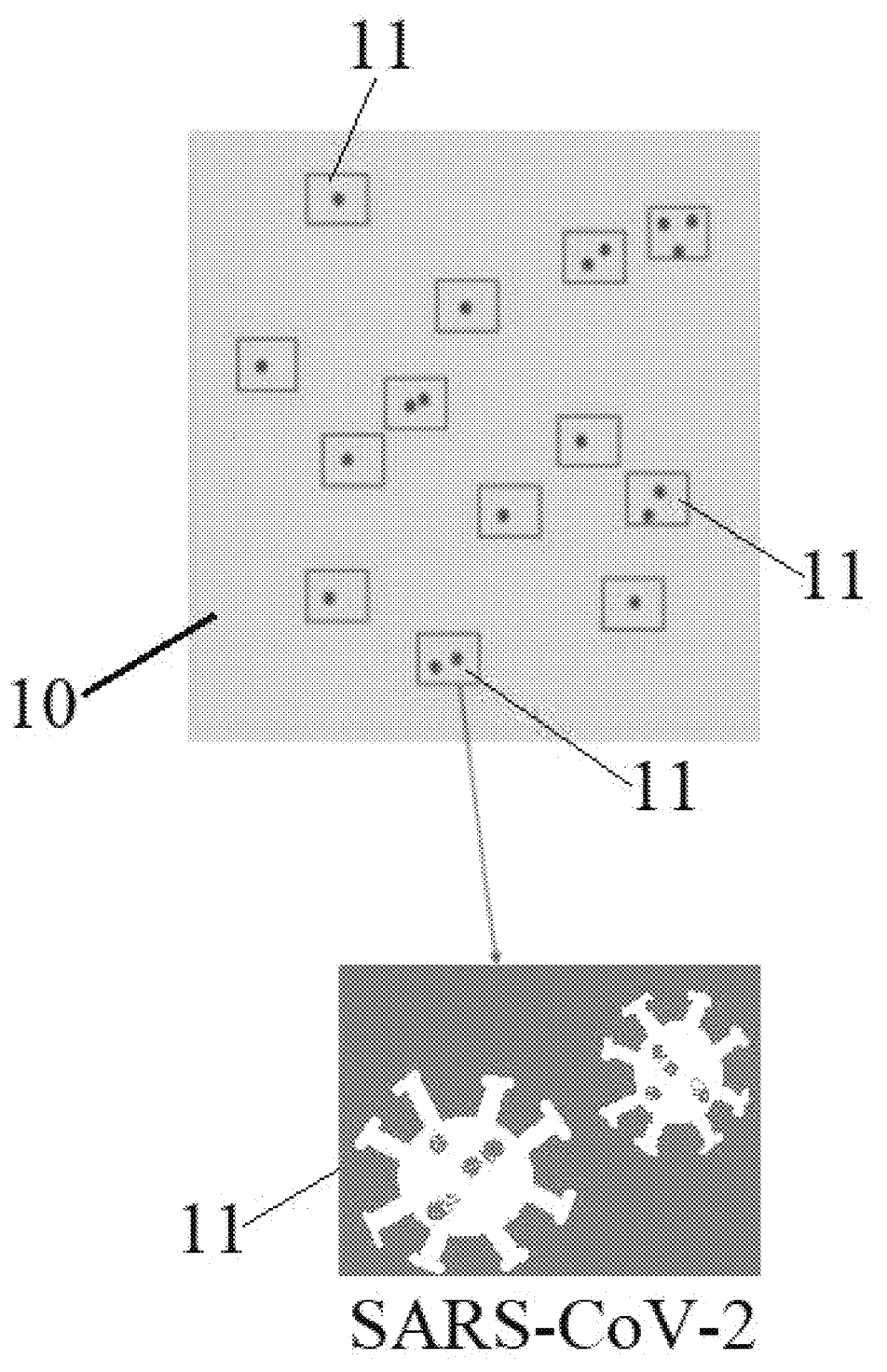

The novel EM column system as shown in FIG. 17 can scan larger FOV with low resolution (like 5, 10 or 20 nm) for the full FOV size. Then, the EM column can switch to high resolution (like 1 nm) automatically without any position and focus change and start immediately to scan high resolution image on any special location. A specific software algorithm can be used to control EM scanning of a larger FOV image with two deflectors (71a, 71b) and co-condensers (3, 4) in a lower resolution mode (i.e. a higher contribution from co-condenser 3 or lower contribution from co-condenser 4). The algorithm will detect related POI (pattern of interesting) and record related location(s). As shown in FIG. 18, the algorithm can detect related POI (pattern of interesting) such as the morphological features of Covid-19 virus (SARS-CoV-2) in a biological sample and record their location(s). Then the software will switch co-condensers (3, 4) to a higher resolution mode (i.e. a lower contribution from co-condenser 3 or a higher contribution from co-condenser 4). The two deflection nodes (71a and 71b) are set to or fixed to a controlled voltage. Other two deflection nodes (72a and 72b) are then used to scan a small FOV 11 with the higher resolution. As shown in the lower panel of FIG. 18, an image of Covid-19 virus (SARS-CoV-2) with a high resolution may be ideally acquired. A software system can combine BSE, DF, BF's images from SEM, TEM, or STEM system and use a machine learning (ML) algorithm to generate an enhanced image with differenced image resolution. Such operations, tasks, and functions are sometimes referred to as being computer-executed, computerized, processor-executed, software-implemented, or computer-implemented. They may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

When implemented in software or firmware, various elements of the systems described herein are essentially the code segments or executable instructions that, when executed by one or more processor devices, cause the host computing system to perform the various tasks. In certain embodiments, the program or code segments are stored in a tangible processor-readable medium, which may include any medium that can store or transfer information. Examples of suitable forms of non-transitory and processor-readable media include an electronic circuit, a semiconductor memory device, a ROM, a flash memory, an erasable ROM (EROM), a floppy diskette, a CD-ROM, an optical disk, a hard disk, or the like.

Through the above description of the embodiments, those skilled in the art can understand clearly that the present application may be implemented by means of software plus necessary hardware platforms, or of course, may also be implemented all by software or hardware. Based on such understanding, the entirety of or a portion of that the technical solutions of the present application contribute over the background art may be embodied in the form of a software product. The computer software product may be stored in storage medium, such as ROM/RAM, disk, optical disk, etc., and comprise several instructions for enabling one computer apparatus (which may be a personal computer, a server, or a network equipment, etc.) to execute the methods described in the respective embodiments or described in certain parts of the embodiments of the present application.

In the foregoing specification, embodiments of the present invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicant to be the scope of the invention, is the literal and equivalent scope of the set of claims that issue from this application, in the specific form in which such claims issue, including any subsequent correction.

The invention claimed is:

1. An apparatus of charged-particle beam comprising a BSE detector, a plasma generator, and a sample stage system;
    wherein the sample stage system includes an upper stage, a lower stage, and a sample table having one or more openings above the upper stage;
    wherein the plasma generator is located below the sample table, and sits onto or partially embedded into the upper sample stage;
    wherein the BSE detector is located above the sample table, and
    wherein the sample table and the plasma generator are so configured that the plasma generator generates plasma and distributes or dissipates the plasma through the one or more openings of the sample table toward and onto surface of the BSE detector.

2. The apparatus of charged-particle beam according to claim 1, further comprising an objective lens above the BSE detector, and a device of limiting aperture that is located above the objective lens.

3. The apparatus of charged-particle beam according to claim 2, wherein the plasma is distributed or dissipated on surfaces of the BSE detector in a concentration higher than that on surface of the device of limiting aperture.

4. The apparatus of charged-particle beam according to claim 1, wherein the plasma generator is configured to periodically generate and distribute the plasma for selectively cleaning contaminants on the surface of the BSE detector.

5. The apparatus of charged-particle beam according to claim 1, wherein the BSE detector has a voltage of 10-25V (e.g. negative voltage) to attract and concentrate the plasma onto their surface for more efficient and selective plasma cleaning.

6. The apparatus of charged-particle beam according to claim 1, wherein the plasma is generated by the application of an electric field, a magnetic field, a microwave, or any combination thereof through a gas selected from oxygen, nitrogen, air, hydrogen, argon, helium, and neon.

7. The apparatus of charged-particle beam according to claim 6, wherein the plasma is generated from air.

8. The apparatus of charged-particle beam according to claim 6, wherein the gas has a nearly vacuum pressure (< or≈1 10 mTorr or 1 Pa), or a low/moderate pressure (>10 mTorr or 1 Pa but<1 Torr or 100 Pa).

9. The apparatus of charged-particle beam according to claim 6, wherein the gas pressure is achieved by controlling a vacuum pump's speed for vacuuming a sample chamber and/or controlling the flow rate of a gas injecting into the sample chamber.

10. The apparatus of charged-particle beam according to claim 1, wherein the plasma is selected from glow discharge plasma, capacitively coupled plasma (CCP), cascaded arc plasma, inductively coupled plasma (ICP), wave heated plasma, or any combinations thereof.

11. The apparatus of charged-particle beam according to claim 1, wherein the plasma generator comprises a source of radio-frequency electrical power, a hollow cylindrical electrode formed of conducting material, and a grounded shield surrounding and enclosing the cylindrical electrode and electrically insulated therefrom;
    wherein the cylindrical electrode is in communication with the source of radio-frequency electrical power, and
    wherein, upon energizing the electrode with a radio-frequency electric power, a plasma is generated from gas in an interior of the cylindrical electrode.

12. The apparatus of charged-particle beam according to claim 11, wherein a central hallow space (or the interior) of the cylindrical electrode is positioned right below one or more of the openings of the sample table, facilitating plasma generated within the central hallow space (or the interior) of the cylindrical electrode to freely travel through the openings and toward the BSE detector.

13. The apparatus of charged-particle beam according to claim 11, wherein the plasma generator further comprises a hollow dielectric cylinder formed of a dielectric material;
    wherein the cylindrical electrode is surrounding an exterior of the dielectric cylinder; and
    wherein, upon energizing the cylindrical electrode with radio-frequency electric power, a plasma is generated from gas in an interior of the dielectric cylinder by radio-frequency, hollow cathode effect coupling inside the dielectric cylinder.

14. The apparatus of charged-particle beam according to claim 13, wherein a central hallow space (or the interior) of the dielectric cylinder is positioned right below one or more of the openings of the sample table, facilitating plasma generated within the central hallow space (or the interior) of the dielectric cylinder to freely travel through the openings and toward the BSE detector.

15. The apparatus of charged-particle beam according to claim 13, wherein the dielectric cylinder is formed of ceramic, glass, quartz, and Teflon such as a machinable ceramic comprising about 55% fluorophlogopite mica and 45% borosilicate glass.

16. The apparatus of charged-particle beam according to claim 13, wherein a virtual anode is formed by the hollow cathode effect along a central axis of the dielectric cylinder in the plasma and a ground is defined by the BSE detector.

17. The apparatus of charged-particle beam according to claim 13, wherein the cylindrical electrode is a brass cylinder around an exterior diameter of the dielectric cylinder.

18. The apparatus of charged-particle beam according to claim 13, further comprising a source of gas in fluid communication with the interior of the dielectric cylinder through a gas flow control device.

19. The apparatus of charged-particle beam according to claim 1, which is an electron microscope (such as TEM), or an electron beam lithography apparatus.

20. A method of selectively cleaning a BSE detector in an apparatus of charged-particle beam, including
    providing an apparatus of charged-particle beam comprising a BSE detector and a sample stage system; wherein the sample stage system includes an upper stage, a lower stage, and a sample table having one or more openings above the upper stage; and wherein the BSE detector is located above the sample table;
    installing a plasma generator in the apparatus of charged-particle beam, wherein the plasma generator is located below the sample table, and sits onto or partially embedded into the upper sample stage; and
    generating plasma with the plasma generator, and distributing or dissipating the plasma through the one or more openings of the sample table toward and onto surface of the BSE detector for selectively cleaning the BSE detector with the plasma.

\* \* \* \* \*